US005507754A

United States Patent [19]
Green et al.

[11] Patent Number: 5,507,754
[45] Date of Patent: Apr. 16, 1996

[54] APPARATUS AND METHOD FOR APPLYING AND ADJUSTING AN ANCHORING DEVICE

[75] Inventors: David T. Green, Westport; Henry R. Sienkiewicz, Stamford; Keith Ratcliff, Sandy Hook; Salvatore Castro, Seymour; Scott E. Manzo, Shelton, all of Conn.

[73] Assignee: United States Surgical Corporation, Norwalk, Conn.

[21] Appl. No.: 109,779

[22] Filed: Aug. 20, 1993

[51] Int. Cl.⁶ .................................................. A61B 17/00
[52] U.S. Cl. ........................ 606/139; 606/144; 112/169
[58] Field of Search ..................................... 606/139, 144, 606/145, 147, 148, 185, 187, 181, 182, 213, 232; 112/169, 80.03; 604/59–62

[56] References Cited

U.S. PATENT DOCUMENTS

| | | | |
|---|---|---|---|
| 1,469,353 | 10/1923 | Benevento | 112/80.03 |
| 2,269,963 | 1/1942 | Wappler | 604/62 |
| 3,103,666 | 9/1963 | Bone . | |
| 3,564,670 | 6/1968 | Bengtsson . | |
| 3,646,929 | 3/1972 | Bonnar . | |
| 4,019,498 | 4/1977 | Hawtrey et al. . | |
| 4,160,453 | 7/1979 | Miller | 606/187 |
| 4,235,238 | 11/1980 | Ogiu et al. . | |
| 4,339,058 | 7/1982 | Wendt | 604/61 |
| 4,448,194 | 5/1984 | De Giovanni et al. | 606/144 |
| 4,491,132 | 1/1985 | Aikins . | |
| 4,614,187 | 9/1986 | Mullhollan et al. | 606/147 |
| 4,621,640 | 11/1986 | Mulhollan et al. . | |
| 4,669,478 | 6/1987 | Robertson . | |
| 4,857,041 | 8/1989 | Annis et al. . | |
| 4,935,027 | 6/1990 | Yoon | 606/148 |
| 5,012,822 | 5/1991 | Schwarz . | |
| 5,013,292 | 5/1991 | Lemay . | |
| 5,019,032 | 5/1991 | Robertson . | |
| 5,036,867 | 8/1991 | Biswas . | |
| 5,080,663 | 1/1992 | Mills et al. | 606/139 |
| 5,085,661 | 2/1992 | Moss | 606/144 |
| 5,109,780 | 5/1992 | Slouf et al. | 112/169 |
| 5,112,344 | 5/1992 | Petros . | |
| 5,123,428 | 6/1992 | Schwarz . | |
| 5,149,329 | 9/1992 | Richardson . | |
| 5,152,749 | 10/1992 | Giesy et al. . | |
| 5,234,454 | 8/1993 | Bangs . | |
| 5,258,015 | 11/1993 | Li et al. . | |
| 5,269,809 | 12/1993 | Hayhurst et al. . | |
| 5,281,197 | 1/1994 | Arias et al. | 604/60 |
| 5,281,237 | 1/1994 | Gimpelson | 606/148 |
| 5,328,077 | 7/1994 | Lou . | |

FOREIGN PATENT DOCUMENTS 9310715  6/1993  WIPO .

OTHER PUBLICATIONS

Richardson, Davis A., et al., "Evolution of Surgery for Stress Urinary Incontinence", Gynecologic Surgery, pp. 191–197, (1988).

Moss Tubes advertisement, *Surgical Products*, Mar. 1993, p. 14.

*Primary Examiner*—Stephen C. Pellegrino
*Assistant Examiner*—Jeffrey A. Schmidt

[57] ABSTRACT

A method and apparatus for elevating, approximating and/or restraining internal organs or structures, and more particularly for treating female urinary stress incontinence is provided. The invention includes an anchoring device having an elongated suture with an anchor at each end thereof and a cinching member therebetween for adjusting the length of the suture, an apparatus for applying the anchoring device, and an apparatus for drawing the suture relative to the cinching member after it has been emplaced. The method involves securing a first anchor to a first structure, such as the vaginal wall, securing a second anchor to a second structure, such as Cooper's ligament, and drawing the suture relative to the cinching member to approximate the first and second anchors, and thereby move the first structure and the second structure into juxtaposition so as to approximate them.

14 Claims, 17 Drawing Sheets

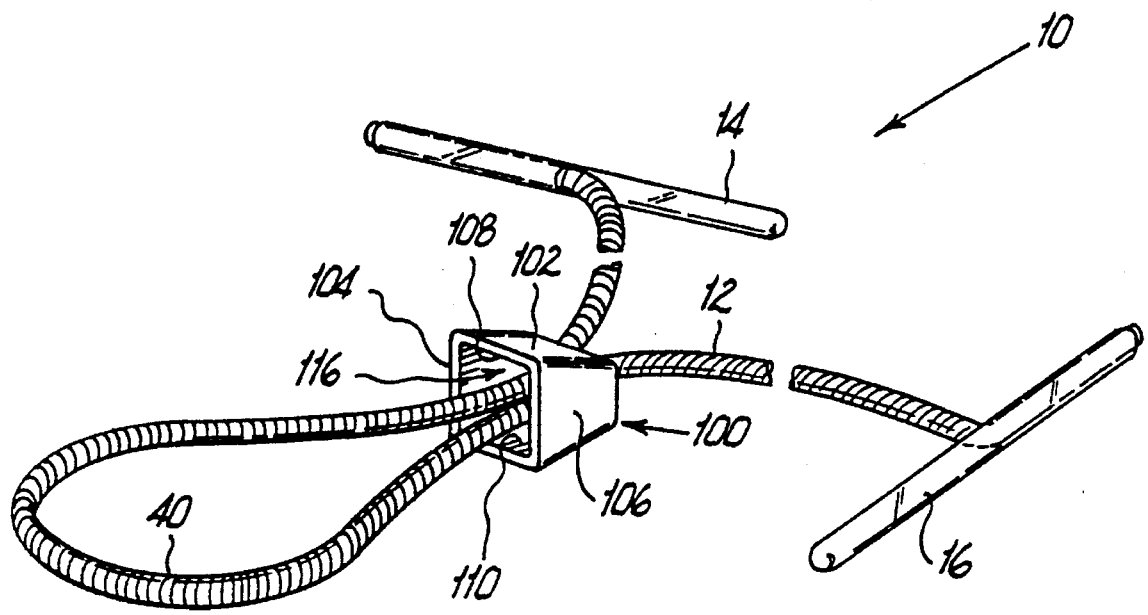
FIG.4
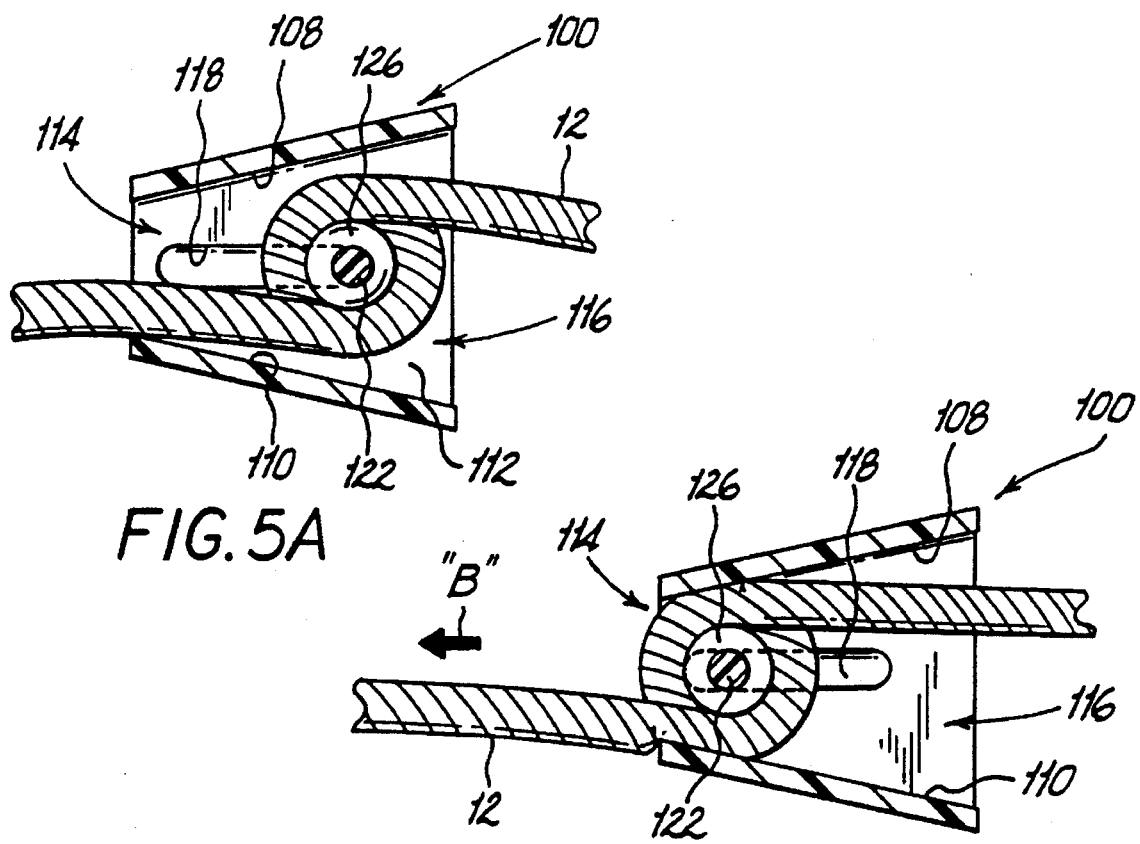
FIG.5A
FIG.5B

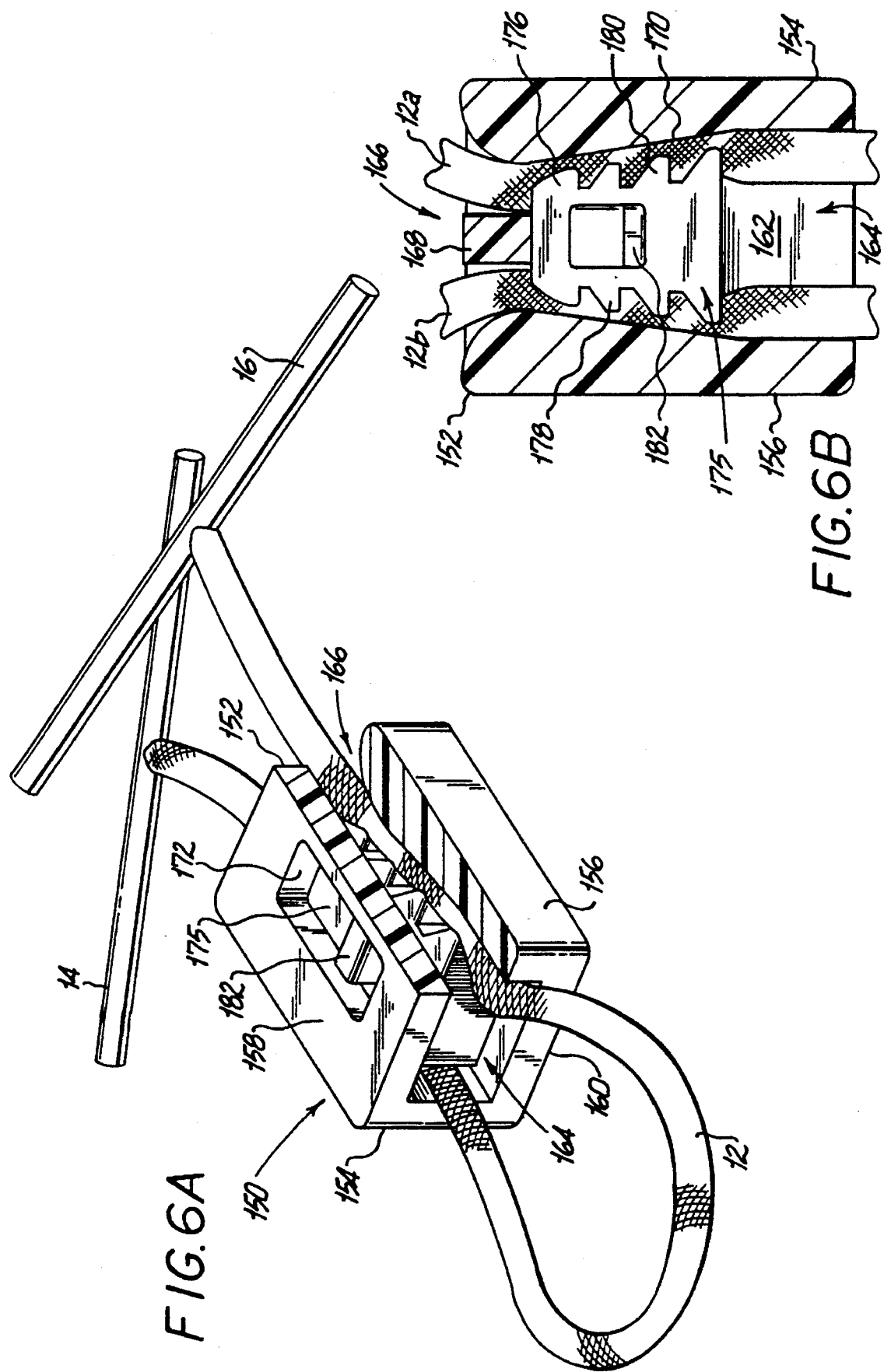

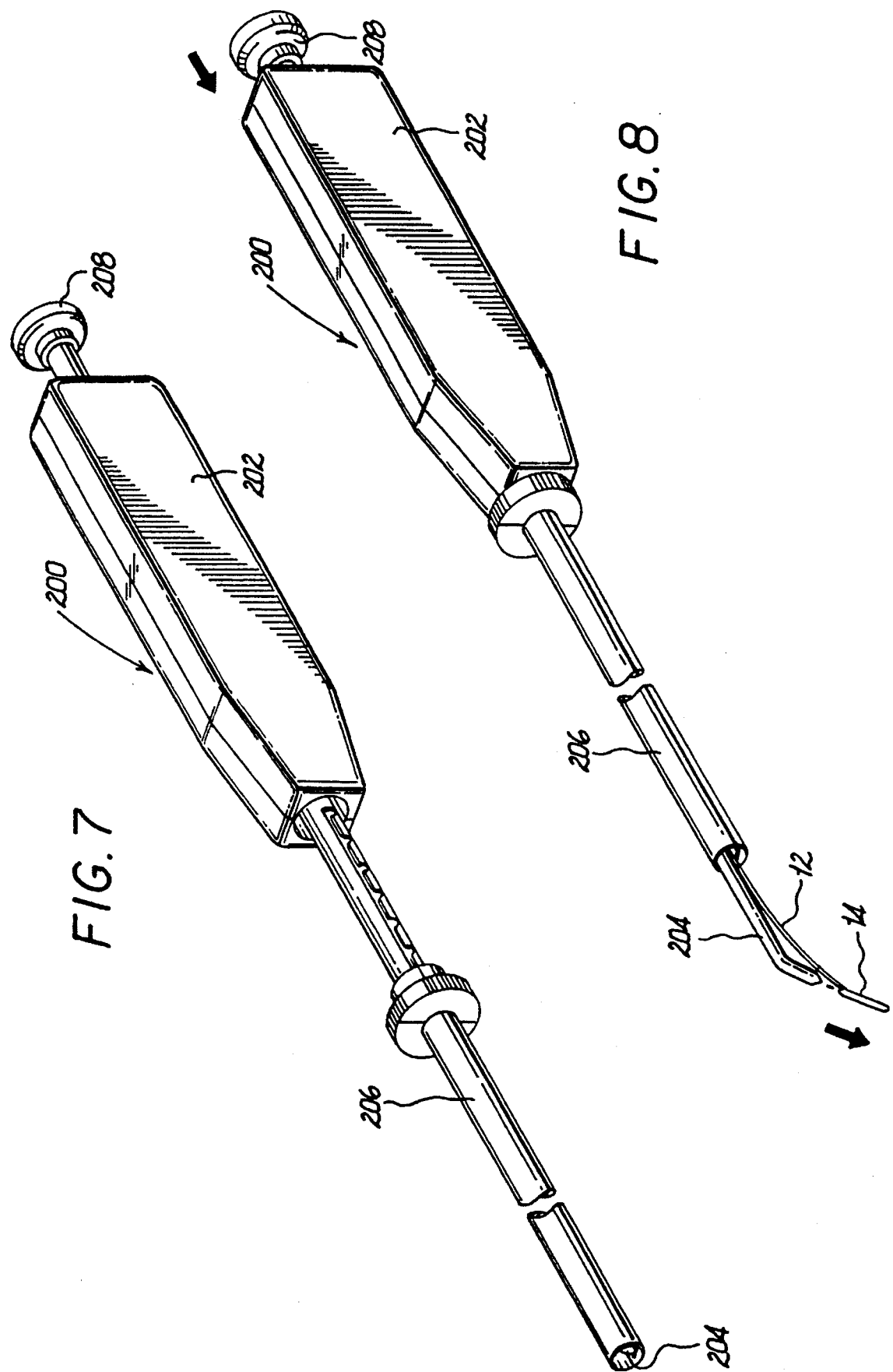

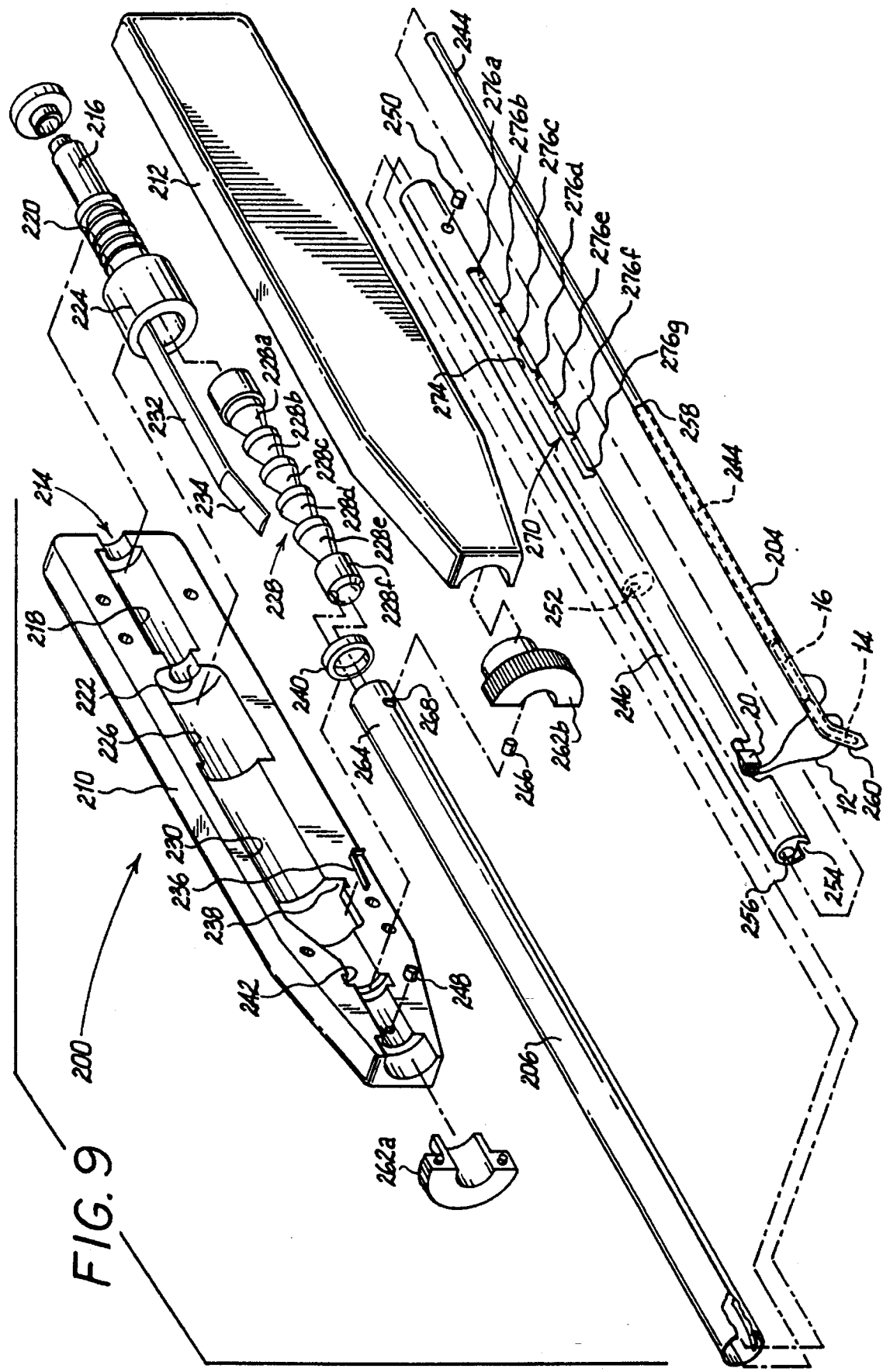

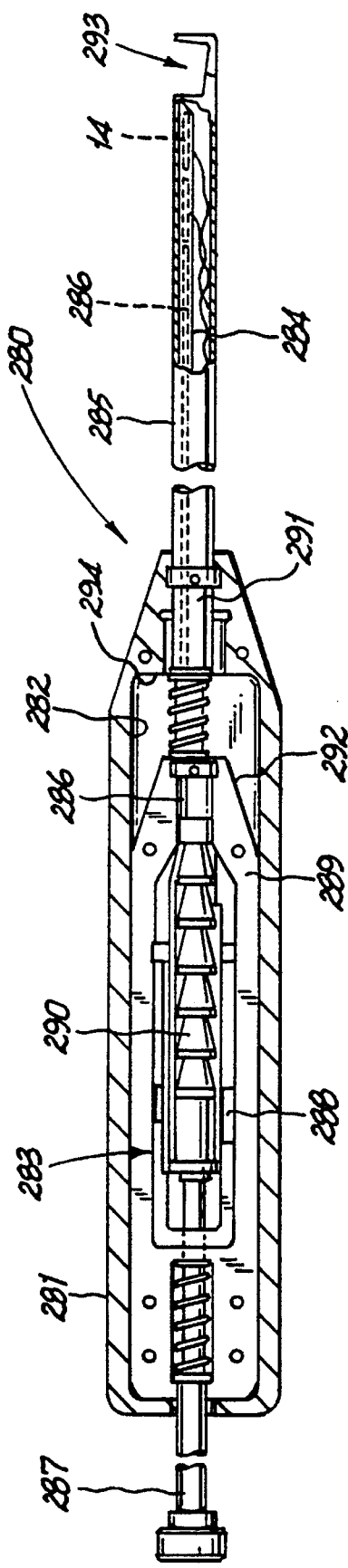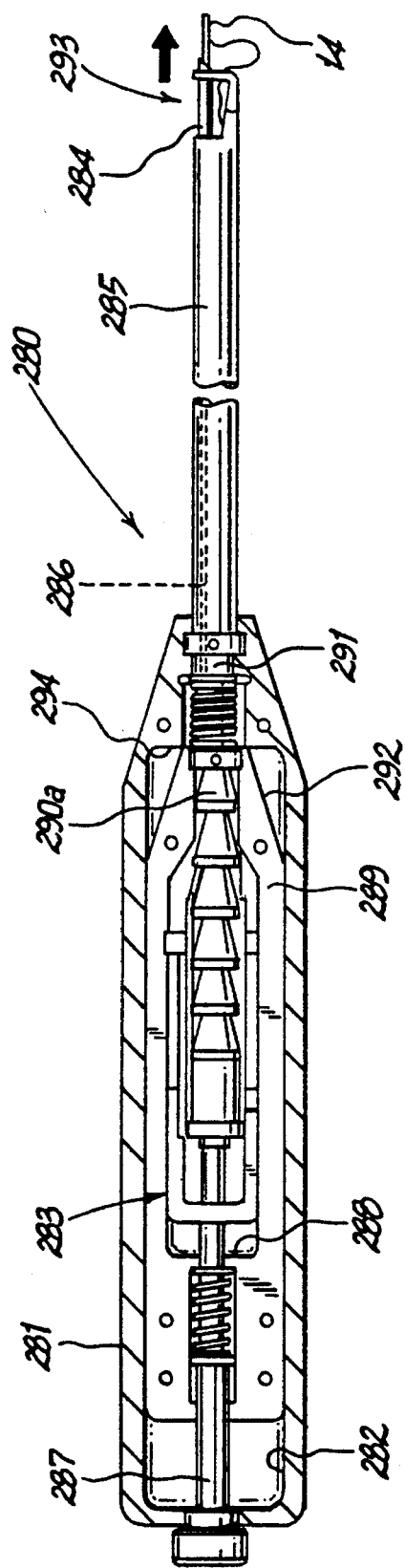
FIG. 14A
FIG. 14B

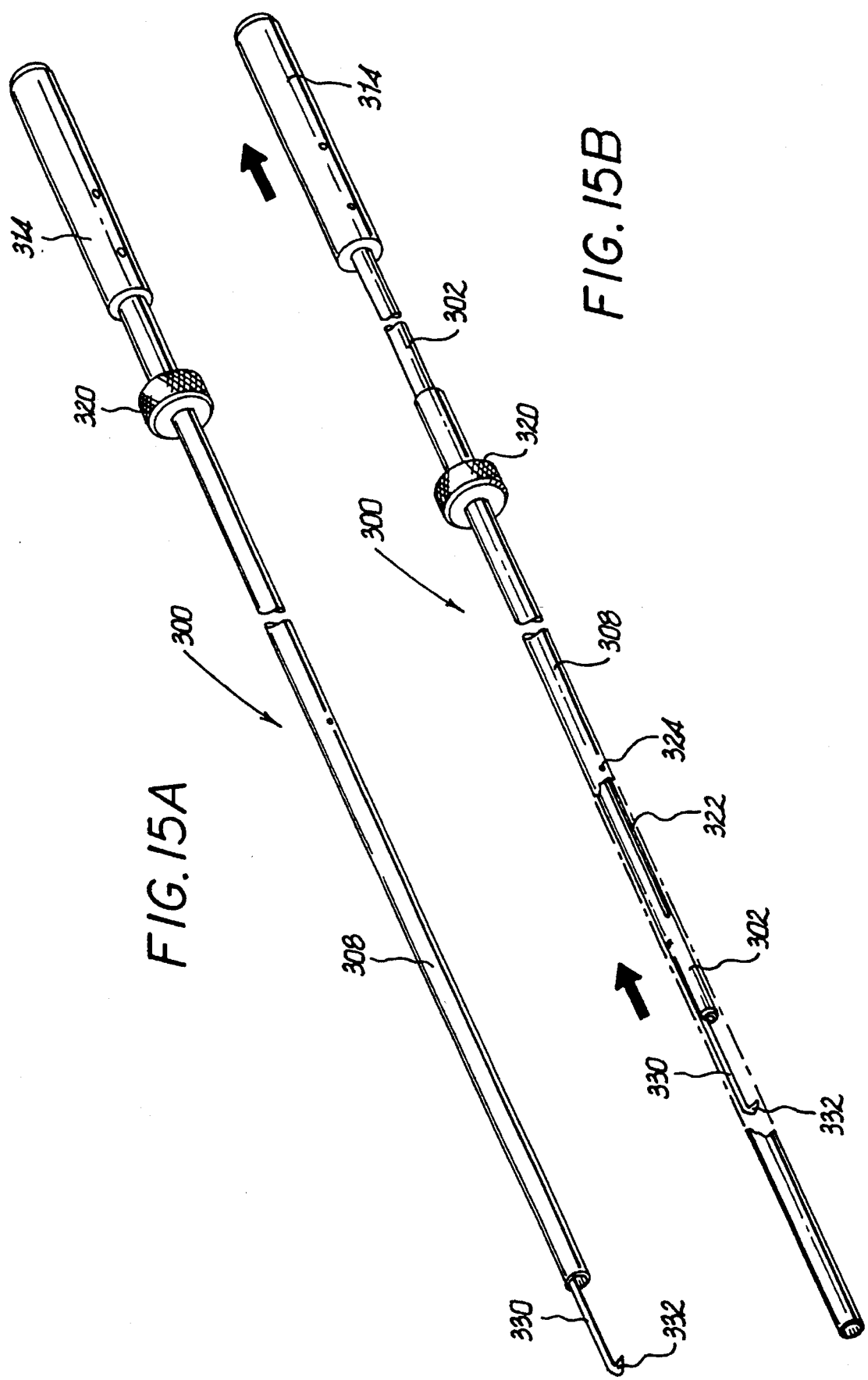

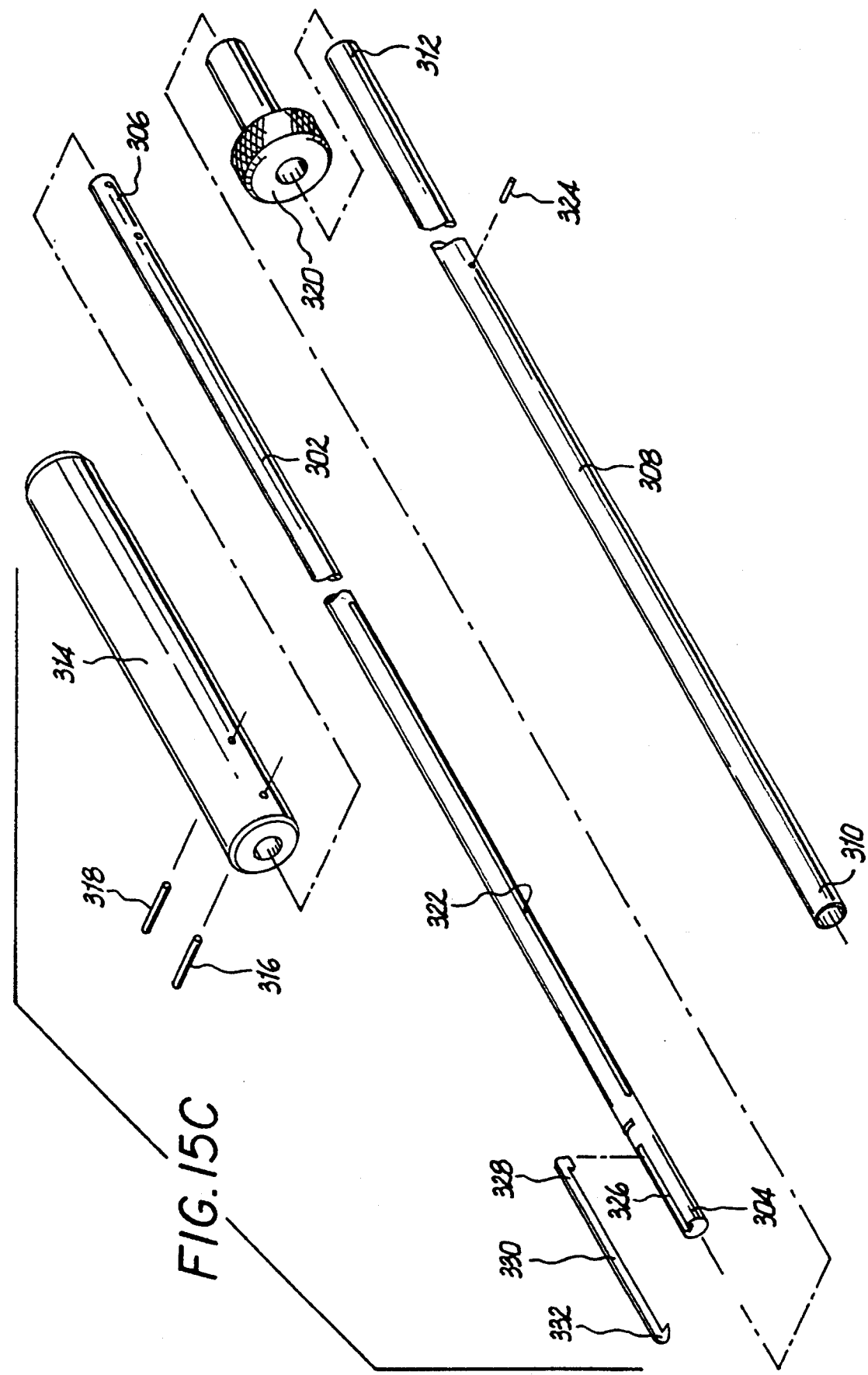

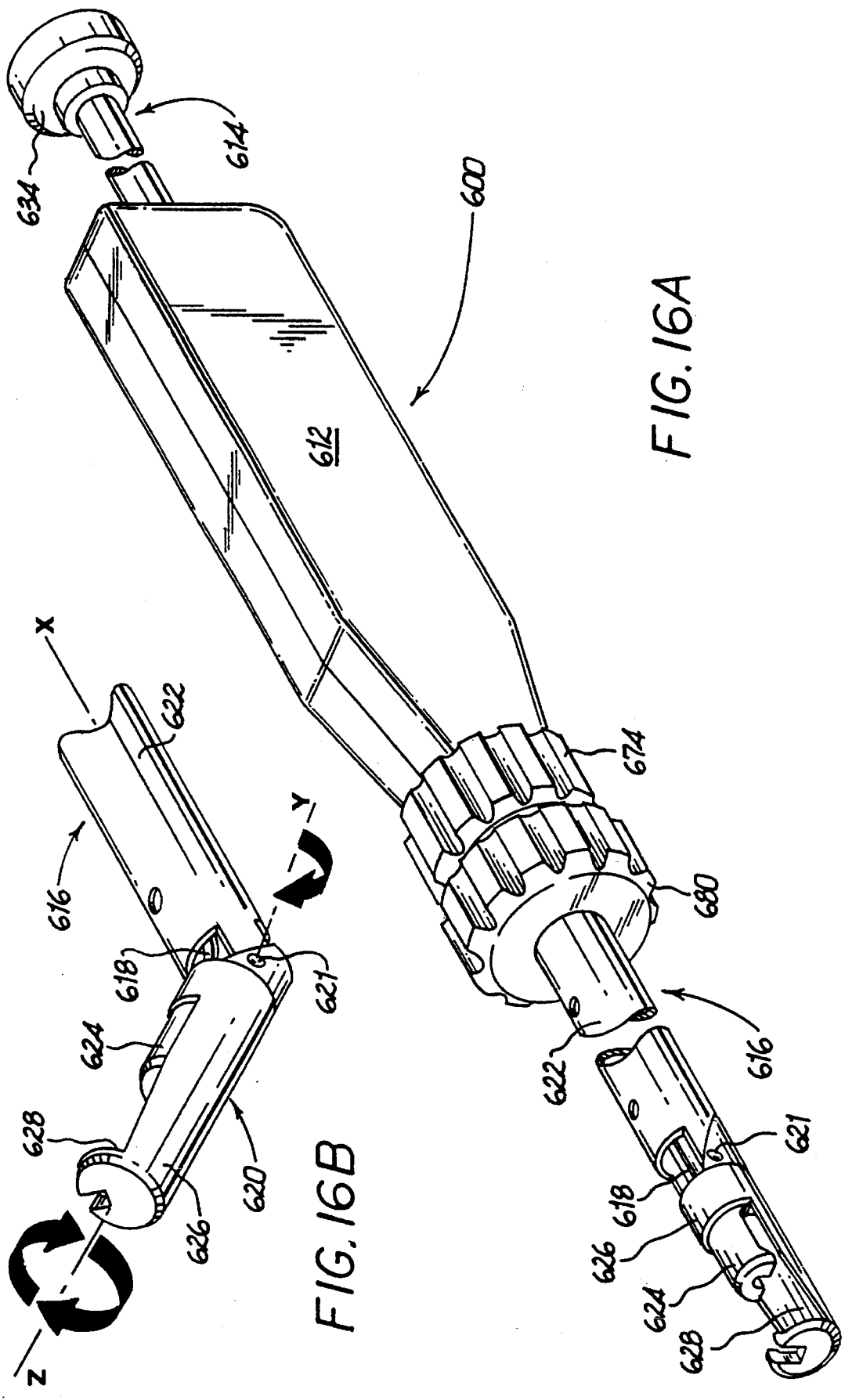

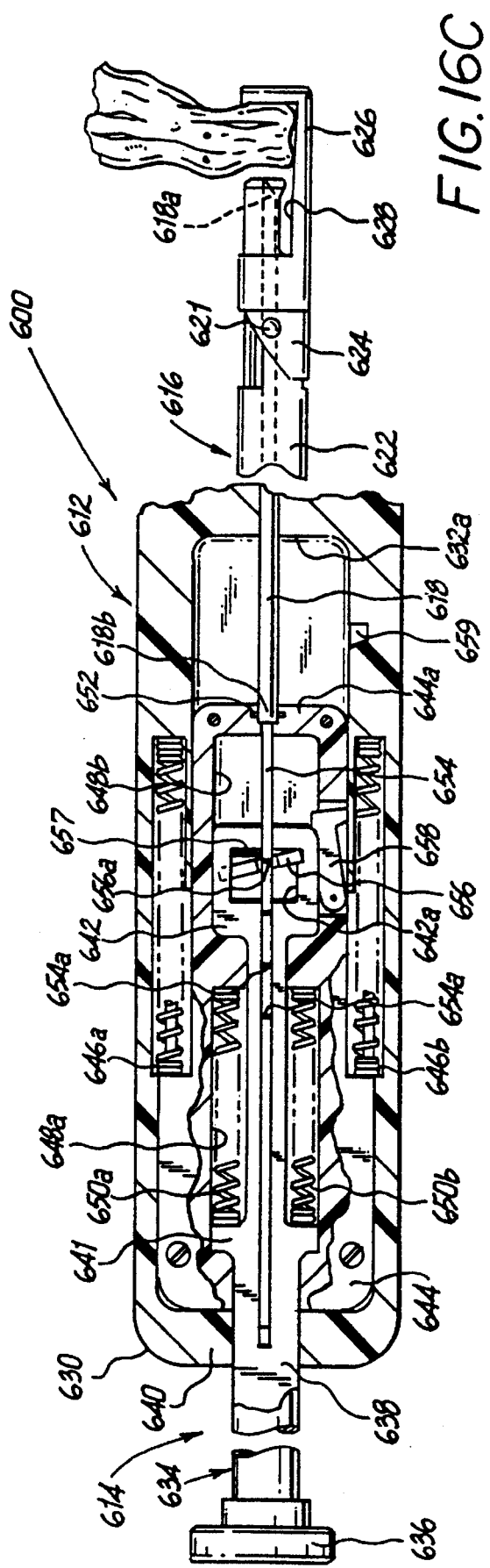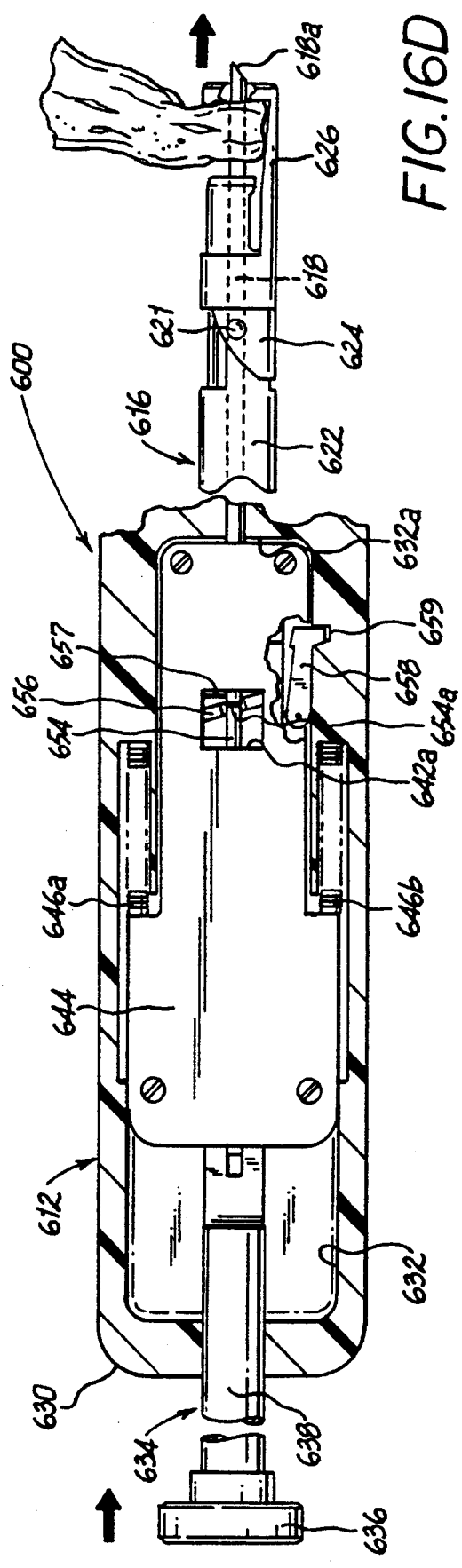

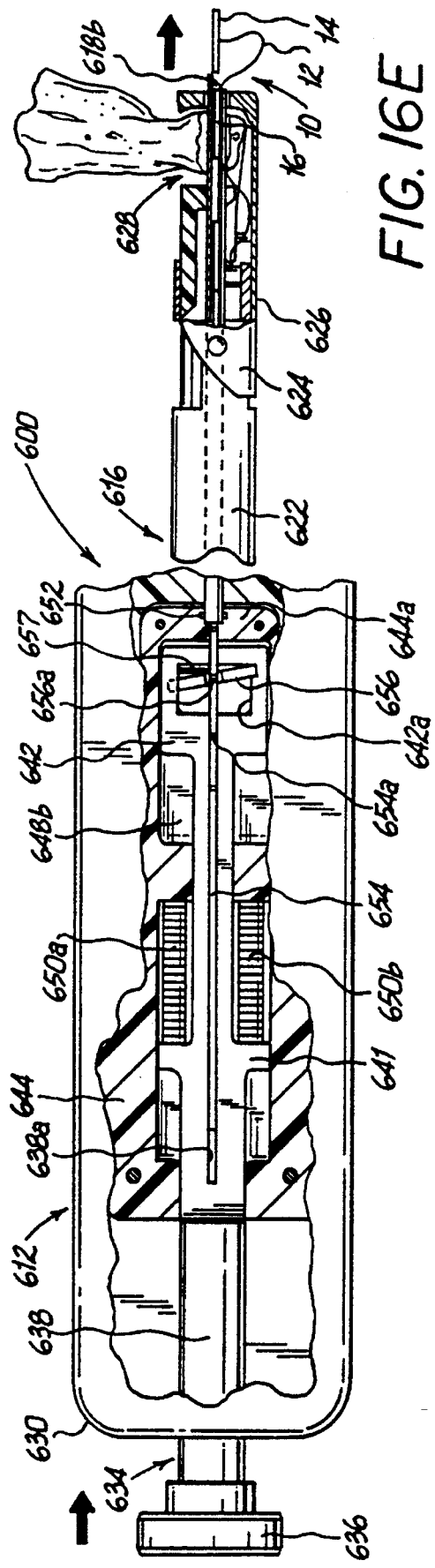
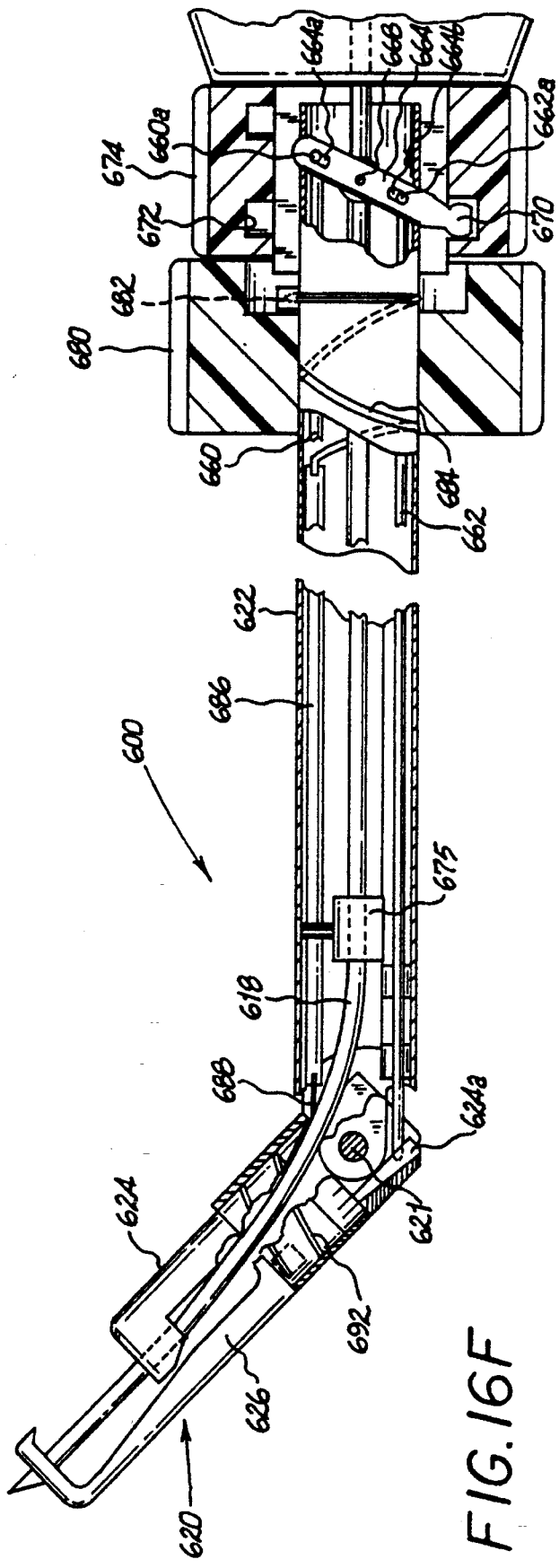

APPARATUS AND METHOD FOR APPLYING AND ADJUSTING AN ANCHORING DEVICE

BACKGROUND OF THE INVENTION

1. Field of the Invention

The present invention relates to an apparatus and method for applying and adjusting a sutured anchoring device. More particularly, this invention relates to an apparatus and a method of elevating the urethrovesical junction relative to the bladder to correct female urinary stress incontinence.

2. Description of Related Art

In females, incontinence, or the inability to control the outflow of urine, can have a variety of causes in the urinary system including congenital defects and defects from trauma or disease. The most common cause of female incontinence is known as stress incontinence and results from weakness or relaxation of the urethral sphincter.

Many procedures, several involving urethrovesical elevation, have been devised over the years, to cure urinary stress incontinence. One early procedure involved fixation of the urethrovesical junction to the symphysis pubis by placing sutures through part of the urethral wall, but caused urethral distortion. A modified version of the procedure involved suturing the urethral lumen directly to the symphysis pubis, and placing additional sutures through the bladder. This technique however, often led to urine loss and/or the formation of bladder stones.

An alternative approach involved attaching the urethrovesical junction to the narrow band of strong aponeurotic fibers which extends laterally along the pectineal line of the pubis commonly referred to as Cooper's ligament. In this procedure which is described in U.S. Pat. No. 5,149,329 to Richardson, the urethrovesical junction is elevated by bringing the paravaginal fascia into juxtaposition with Cooper's ligament through suture placement.

A number of procedures for urethrovesical elevation involve anchoring the paravaginal fascia to the abdominal wall. See, for example, U.S. Pat. No. 5,112,344 to Petros which describes looping a filamentary element between the vaginal wall and the rectus abdominis in the anterior wall of the abdomen whereby it passes to each side of the urethra to correct the spacial relationship to the pubis. U.S. Pat. No. 5,019,032 to Robertson describes a method of treatment involving the installation of sutures between the rectus fascia and the vagina by means of a needle inserted through the abdomen.

A sling procedure is disclosed in U.S. Pat. No. 5,013,292 to Lemay and describes a method for correcting female urinary incontinence by implanting a sling-like anchoring device in the skin above the symphysis pubis to adjust the urethrovesical angle. The anchoring device includes a pair of implants each having a head portion adapted to rest on the symphysis pubis and a suture portion connected to the head portion. The head portion is shaped as a figure eight having a central crossbar about which a central portion of the suture is wrapped. Utilizing a bendable needle inserted through the vaginal mucosa, the head portion of each implant is embedded in the skin over the symphysis pubis and the sutures are tied together to support the urethrovesical junction. Alternatively, the ends of the sutures can be tied to a saddle member configured to support the bladder neck.

Such invasive surgical procedures have also been utilized in other areas of the body, including surgery on the gall bladder, appendix, lungs and the like. For the reasons previously stated, the use of laparoscopic and endoscopic surgical procedures have been relatively popular and such popularity has provided additional incentive to develop the procedures further.

In laparoscopic procedures, surgery is performed in the interior of the abdomen through a small incision e.g., through narrow tubes inserted through small entrance wounds in the skin; and in endoscopic procedures, surgery is performed in any hollow viscus of the body. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments used in such procedures be long and narrow while being functionally controllable from one end of the instrument, i.e., the proximal end.

Up to the present there remains a need for an apparatus which is particularly adapted to endoscopically apply sutured anchors to body tissue in a manner to positively secure the sutured anchor to the body tissue without danger of separation thereof after suspension or, in the case of fascia closure is completed. There is also a need in the surgical arts for an improved apparatus to elevate and/or restrain internal organs or structures. In particular, there remains a need to achieve urethrovesical elevation. The present invention relates to such a sutured anchor member, an apparatus for applying the sutured anchor member and a method for attaching and adjusting the sutured anchor member particularly configured and adapted to accomplish these objectives.

SUMMARY OF THE INVENTION

An apparatus for applying an anchoring device to body tissue preferably comprises a handle portion defining a longitudinal axis, an elongated needle body extending from the handle portion and defining an axial bore configured to retain the anchors of the anchoring device, an elongated housing mounted adjacent the needle body and longitudinally movable with respect thereto between a first position wherein a distal end portion of the needle body is extended from the housing and a second position wherein the distal end portion of the needle body is shielded by the housing. The apparatus also includes means operatively associated with the handle portion for individually advancing the anchors from the distal end portion of the needle body. Preferably, the means for individually advancing the anchors from the needle body comprises an axially advanceable ratchet assembly which includes an elongated rack member, engaging means for locking the rack member in a predetermined axial position, a selectively actuable driving arm configured to interact with the rack member to advance the rack member in a distal direction, and a push rod extending within the needle body and from a distal end of the rack member for advancing the anchors therefrom.

In a preferred embodiment of the subject invention, the anchoring device comprises an elongated suture having an anchor positioned at each end thereof, and means provided on the suture and movable with respect thereto for adjusting the operative length of the suture. Preferably, each anchor is positioned orthogonal to the elongation of the suture. The operative length of the suture is preferably adjusted by a cinching member positioned proximate a medial portion of the suture and formed by a housing having a passageway extending therethrough for receiving a looped portion of the suture. Gripping means is operatively associated with the passageway for controlling movement of the cinching member with respect to the suture in a first direction and inhibiting movement of the cinching member with respect to the suture in a second direction. The gripping means can comprise a deflectable suture gripping plate positioned within the passageway or, in the alternative, a translating roll bar positioned within the passageway and movable between a disengaged position and an engaged position.

Another aspect of the overall invention is an apparatus for adjusting the operative length of the anchoring device, and more particularly, drawing the suture relative to the cinching member preferably comprises a tubular outer housing which defines a longitudinal axis, a tubular inner shaft mounted for coaxial movement with respect to the outer housing, means for maintaining the radial alignment of the inner shaft with respect to the outer housing relative to the longitudinal axis thereof, and means positioned at a distal end portion of the inner shaft for engaging a suture. Preferably, the means for maintaining the angular orientation of the inner shaft with respect to the outer housing includes an elongated guide slot formed in the inner shaft and a transverse guide pin mounted in the outer housing for communicating with the guide slot. The means for engaging a suture preferably comprises a rigid hook member mounted at the distal end of the inner shaft.

A method is disclosed for correcting female urinary stress incontinence by elevating the urethrovesical function relative to the bladder by bringing the vaginal wall into juxtaposition with Cooper's Ligament. The method comprises the steps of: providing an anchoring device including an elongated suture having a first anchor at one end thereof, a second anchor at the opposed end thereof and means for cinching the suture disposed therebetween; securing the first anchor to a first structure, e.g., the vaginal wall; securing the second anchor to a second structure, e.g., Cooper's ligament; and drawing the suture relative to the cinching means to approximate the first and second anchors. In the context of the treatment of female urinary stress incontinence, one anchor elevates the urethrovesical junction relative to the bladder by approximating the vaginal wall with respect to Cooper's ligament.

Preferably, the step of securing the first anchor in the vaginal wall comprises inserting the needle through the vaginal wall, deploying an anchor, withdrawing the needle from the vaginal wall at a location spaced from the point of insertion, and subsequently emplacing the anchor exterior of the vaginal wall. The step of securing the second anchor preferably comprises extending the anchor through Cooper's ligament from a posterior surface thereof to an anterior surface thereof, and emplacing the anchor adjacent the anterior surface of Cooper's ligament. The step of drawing the suture relative to the cinching means preferably comprises engaging a loop formed in the suture adjacent the cinching member and subsequently drawing the suture loop through the cinching means to approximate the first and second anchors.

The method for surgically treating female urinary stress incontinence may also comprise the steps of: providing an anchor placement apparatus including a needle body defining a bore in which the first and second anchors are retained, and providing an apparatus for drawing the suture relative to the cinching member. The step of securing the first anchor to the vaginal wall is accomplished by inserting the distal end of the needle body into the vaginal wall, extending the needle body from the vaginal wall at a location spaced from the point of insertion, and subsequently advancing the first anchor from the distal end of the needle body to emplace the anchor exterior of the vaginal wall. The second anchor is then secured to Cooper's ligament by extending the needle body through Cooper's ligament from a posterior surface thereof to an anterior surface thereof, and subsequently advancing the second anchor from the distal end of the needle body to emplace the second anchor adjacent the anterior surface of Cooper's ligament. The loop formed in the suture adjacent the cinching means is engaged with the retractable hook provided at the distal end of the suture drawing apparatus. Retracting the hook draws the suture relative to the cinching means and thereby approximates the first and second anchors to bring the vaginal wall and Cooper's ligament into juxtaposition so as to elevate the urethrovesical junction relative to the bladder.

Although the method of the invention has been described above primarily in the context of the treatment of female urinary stress incontinence, the novel method of the invention may find applicability in a variety of clinical settings where it is desired to elevate, approximate and/or restrain one or more organs or structures. Further features of the method and apparatus of the subject invention will become more readily apparent from the following detailed description of the invention taken in conjunction with the drawings.

BRIEF DESCRIPTION OF THE DRAWINGS

So that one skilled in the art to which the subject invention appertains will better understand how to make and use the invention, preferred embodiments of the method and apparatus will be described hereinbelow with reference to the drawings wherein:

FIG. 4 is a perspective view of another anchoring device constructed in accordance with a preferred embodiment of the subject invention;

FIG. 5 is a side elevational view in partial cross-section of the cinching member of the anchoring device of FIG. 4 as the suture is moved relative thereto;

FIG. 6 is a side elevational view in partial cross-section of the cinching member of the anchoring device of FIG. 4 with the suture in a stationary position with respect thereto;

FIG. 7 is a perspective view of an apparatus constructed in accordance with a preferred embodiment of the subject invention for applying the anchoring device illustrated in FIGS. 1 and 4 during a surgical procedure;

FIG. 8 is a perspective view of the anchor applying apparatus of FIG. 7 illustrating the deployment of an anchoring device constructed in accordance with a preferred embodiment of the subject invention;

FIG. 9 is an exploded perspective view of the anchor applying apparatus of FIG. 7;

FIG. 14A is a side elevational view in cross-section of another anchor applying apparatus constructed in accordance with a preferred embodiment of the subject invention prior to actuation;

FIG. 14B is a side elevational view in cross-section of the anchor applying apparatus of FIG. 14A in a fully actuated position;

FIG. 15A is a perspective view of an apparatus constructed in accordance with a preferred embodiment of the subject invention for adjusting the operative length of the anchoring device of FIGS. 1 and 4 during a surgical procedure;

FIG. 15B is a perspective view in partial cross-section of the FIG. 15A illustrating the movement of the inner shaft relative to the outer housing thereof;

FIG. 16 is an exploded perspective view of the apparatus of FIG. 15A;

DETAILED DESCRIPTION OF THE PREFERRED EMBODIMENTS

Figure 1:
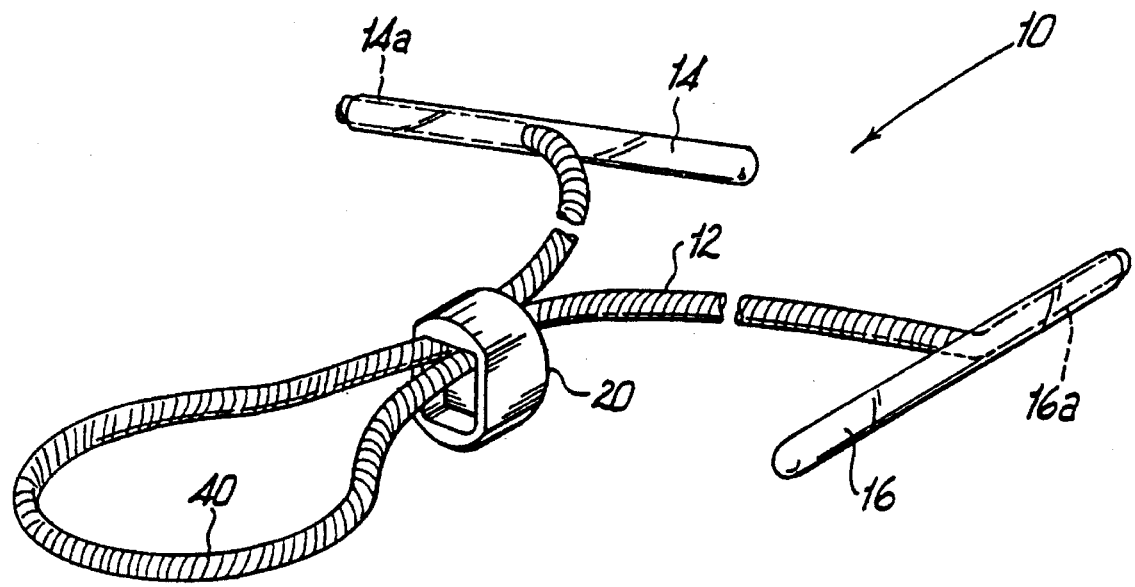
FIG. 1 is a perspective view of a surgical anchoring device constructed in accordance with a preferred embodiment of the subject invention.

In the drawings and in the description which follows, the term "proximal", as is traditional, will refer to the end of the apparatus which is closest to the operator, while the term "distal" will refer to the end which is furthest from the operator.

I. OVERVIEW OF THE SUBJECT INVENTION

The overall objective of the method and apparatus of the subject invention is to apply a pair of sutured anchors to a body organ or structure and adjust the relative positions of the two structures through which the sutured anchors have been placed. More particularly, the apparatus and method of the present invention may be used to elevate, approximate and/or restrain one or more organs or structures and is especially applicable to suspending the neck of the bladder by elevating the urethrovesical junction relative to the bladder. Referring in general to the figures, to more easily facilitate the method, the subject invention may include three devices for performing this procedure: an adjustable anchoring device 10, an apparatus for applying the anchoring device to body tissue 200, and an apparatus for adjusting the length of the anchoring device after it has been emplaced 300. The following is a brief description of each of the three devices and the manner in which each is employed, although other devices may be substituted for or used in combination with these devices to perform the application of and/or approximation of the anchoring device. A detailed description of each device and the method of elevating an exemplary structure, namely the urethrovesical junction relative to a bladder, will follow thereafter.

Briefly, the adjustable anchoring device 10 comprises an elongated suture having a rigid anchor disposed at each end thereof, and a cinching member 20 associated therewith and which is configured to prevent movement of the suture to adjust the operative length thereof. The apparatus 200 for applying the anchoring device 10 includes a handle portion from which extends an elongated needle body configured to retain the anchors, and a ratcheting mechanism for individually advancing the anchors from the needle body. The apparatus 300 for adjusting the operative length of the anchoring device 10 comprises a telescoping tubular assembly having a retractable hook associated therewith configured to engage a looped portion of the suture disposed adjacent the cinching member. Operation of the apparatus will effect relative movement of the suture and cinching member to vary the length of the suture and thereby approximate the ends thereof.

II. THE ANCHORING DEVICE

Figure 2:
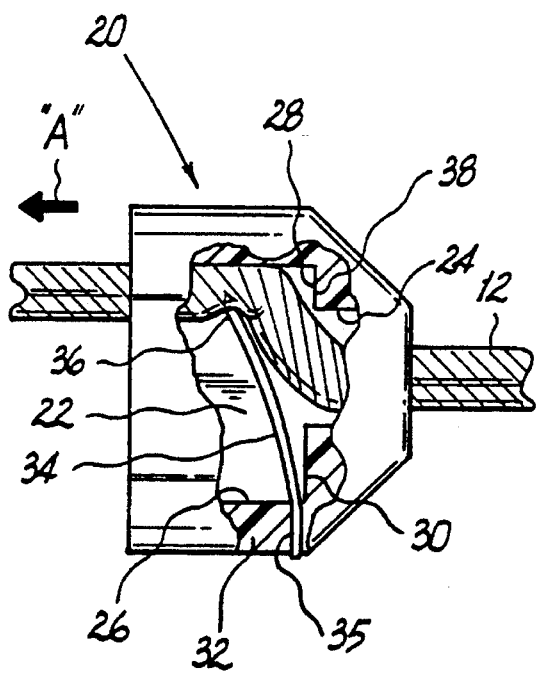
FIG. 2 is a side elevational view in partial cross-section of the cinching member of the anchoring device of FIG. 1 as the suture is moved relative thereto.
Figure 3:
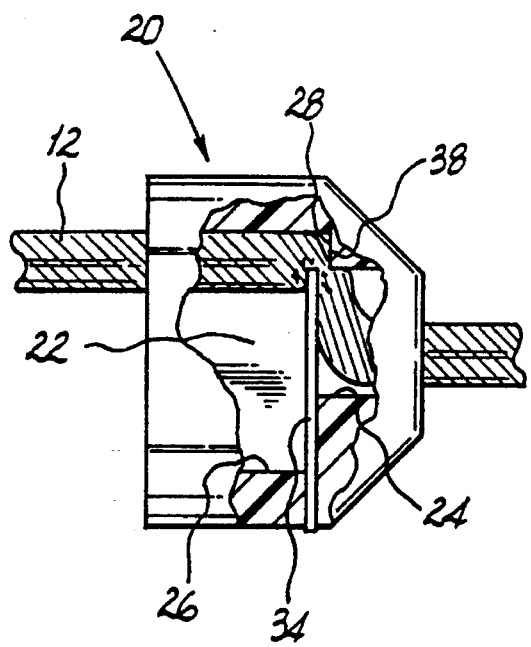
FIG. 3 is a side elevational view in partial cross-section of the cinching member of the anchoring device of FIG. 1 with the suture in a stationary position with respect thereto.
Figure 10:
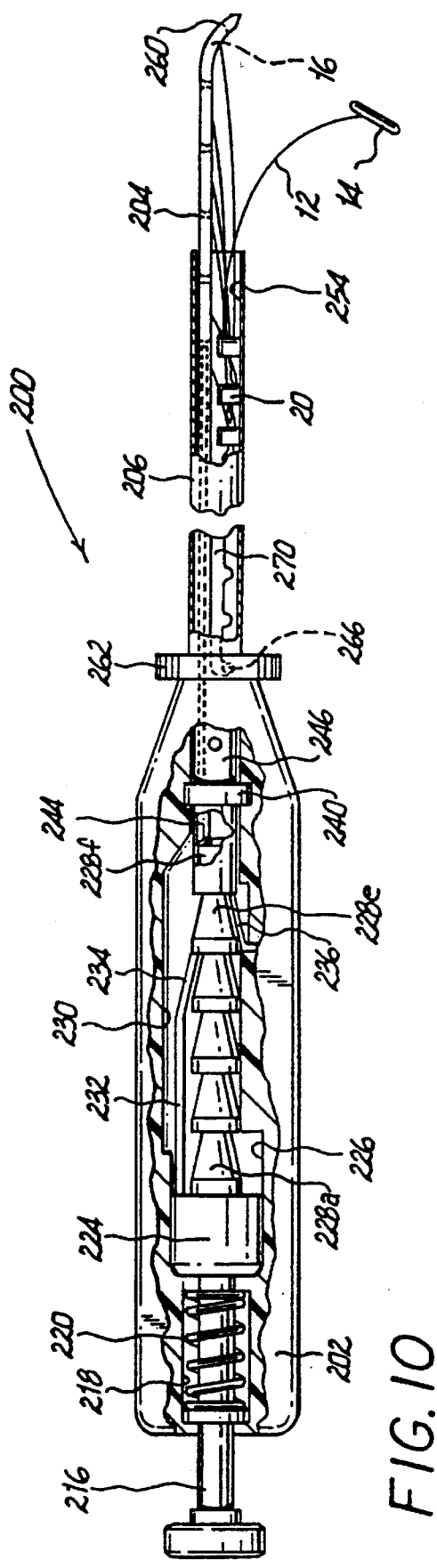
FIG. 10 is a side elevational view in partial cross-section of the anchor applying apparatus of FIG. 7 prior to actuation.

Referring to FIGS. 1–3, an anchoring device constructed in accordance with a preferred embodiment of the subject invention is illustrated and is designated generally by reference numeral 10. The anchoring device 10 includes an elongated suture 12 having a first anchor 14 at one end thereof and a second anchor 16 at the opposed end thereof. Anchors 14 and 16 are preferably substantially orthogonal to the elongation of suture 12, and are formed of a biocompatible material. The material preferably is formed of titanium, but may also be a rigid plastic or stainless steel. Preferably, anchors 14 and 16 are formed with internal bores 14a and 16a, respectively, for receiving and retaining the end portions of suture 12, as illustrated in FIG. 1. However, the anchors may be insert molded or fastened to the ends of the suture by other methods known in the art, such as, for example, adhesive bonding or sonic welding. Alternatively, the anchors may be integrally formed with the suture portion of the device.

A cinching member 20 is positioned on suture 12 between anchors 14 and 16 for adjusting the operational length of the suture 12, and more particularly, for facilitating approximation of the anchors 14 and 16 provided at each end thereof. As best shown in FIG. 2, the cinching member 20 has a stepped axial passageway 22 defining a leading section 24 and a trailing section 26. The leading section 24 has a diameter which is less than that of the trailing section 26. Transverse buttressing walls are formed within passageway 22 and include a forward wall 28 and a rearward wall 30. A transverse slot 35 is formed in the housing wall 32 of cinching member 20, in line with the rearward wall 30, for receiving and retaining a deflectable gripping plate 34. The gripping plate 34 operatively separates the leading section 24 and the trailing section 26 of passageway 22. Further-more, the relative orientation of the forward wall 28 with respect the rearward wall 30 creates a gap between the free edge 36 of gripping plate 34 and the internal edge 38 of forward wall 28. This gap permits the extension of suture 12 through passageway 22.

In operation, the application of a tensile force on, or linear movement of, suture 12 in the direction indicated by arrow "A" in FIG. 2, will cause the gripping plate 34 to deflect away from the forward buttressing wall 28, enlarging the gap therebetween, and permitting substantially unobstructed movement of suture 12 in direction "A" relative to the stationary cinching member 20. In contrast, in the absence of an applied force along the length of suture 12, as shown for example in FIG. 3, the gripping plate 34 will remain parallel with the forward buttressing wall 28 and the gap therebetween will be at a minimum, thereby inhibiting movement of suture 12 relative to cinching member 20.

Preferably, as illustrated in FIG. 1, the cinching member 20 is initially positioned at the mid section of suture 12 in such a manner so that a loop 40 is formed in suture 12 adjacent the trailing section 26 of passageway 22. In use, as the suture loop 40 is drawn relative to the cinching member 20, the anchors 14 and 16 positioned at the opposed ends of suture 12 will approximate toward one another, thereby curtailing the operative length of the suture 12.

Referring to FIGS. 4–6, another cinching member constructed in accordance with a preferred embodiment of the subject invention is illustrated and is designated generally by reference numeral 100. Cinching member 100 comprises a housing 102 having opposed parallel side walls 104 and 106 and converging upper and lower bearing walls 108 and 110. A passageway 112 extends through the housing 102 from an inlet port 114 to an outlet port 116. The outlet port 116 defines an aperture which is smaller than the aperture defined by the inlet port 114. An elongated slot 118 is defined in the internal surface of side wall 104 and a corresponding slot (not shown) is formed in the internal surface of side wall 106. The slots are configured to retain the axle pin 122 of a transverse roller bearing 126.

Roller bearing 126 is dimensioned to have suture 12 wrapped thereabout in such a manner so as to create looped portion 40 adjacent the outlet port 116 as best seen in FIGS. 4–6. In use, the roller bearing 126 is movable between a non-engaging position adjacent the inlet port 114 (see FIG. 5) and an engaging position adjacent the outlet port 116 wherein the roller bearing 126 compresses the suture 12 against the bearing walls 108 and 110 of housing 102 to secure the position of cinching member 100 with respect to the suture 12 (see FIG. 6). To adjust the length of suture 12 and thereby approximate the opposed ends thereof, the looped portion 40 of suture 12 is drawn through passage 112, in the direction indicated by arrow "B" in FIG. 6, until a desired operative suture length is achieved. During this suture adjustment period, the roller bearing is maintained in its engaging position and rotates to accommodate the movement of suture 12 relative thereto. It will be readily apparent to those skilled in the art to which the subject invention appertains that other mechanisms for cinching the suture may otherwise be provided.

III. APPARATUS FOR APPLYING THE ANCHORING DEVICE

Referring to FIGS. 7–13, a surgical apparatus for applying the anchoring device 10 is illustrated and is designated generally by reference numeral 200. In brief, surgical apparatus 200 comprises a handle portion 202, an elongated needle body 204 extending from the handle portion 202 and configured to retain anchors 14 and 16, a sheath 206 mounted adjacent needle body 204 and configured to move longitudinally with respect thereto. An actuation mechanism designated generally by reference numeral 208 is operatively associated with the handle portion 202 for effectuating the individual advancement of anchors 14 and 16 from the needle body 204, as illustrated, for example, in FIG. 8.

Turning to FIG. 9, the handle portion 202 of surgical apparatus 200 includes hemi-sections 210 and 212 adapted to be mounted to one another and defining a compartmented axial bore 214 configured to accommodate various elements associated with actuation mechanism 208. The actuation mechanism 208 includes a plunger 216 dimensioned for retention within the proximal compression chamber 218 of axial bore 214. A coiled return spring 220 is coaxially disposed about plunger 216 and is positioned against the distal wall 222 of chamber 218 for biasing the plunger 216 in a proximal direction. A cylindrical drive shaft 224 extends from the distal end of plunger 216 and is accommodated within a primary drive chamber 226 of axial bore 214.

Drive shaft 224 communicates with a segmented ratchet shaft 228 which is operatively disposed within a secondary drive chamber 230 of axial bore 214. Ratchet shaft 228 is defined by a plurality of ratchet segments 228a–228f each of similar configuration. The ratchet segments 228a–228f are also of equal length and the length of each corresponds to the length of each of the anchors retained within needle body 204. Thus, as each segment of ratchet shaft 228 is advanced a distance equal to its length, so to are the anchor members disposed within the needle body 204. See generally, FIGS. 10–13.

With continuing reference to FIG. 9, the actuation mechanism 208 further comprises an elongated drive arm 232 which extends from the drive shaft 224 and which includes an angularly depending distal portion 234 configured to selectively engage the segmented ratchet shaft 228 and drive it in a distal direction in response to movement of plunger member 216. The distance of the compression stroke of plunger 216 also corresponds to the length of each segment of ratchet shaft 228. A locking beam 236 resides in a cavity 238 adjacent the distal end of the secondary drive chamber 230 for securing the axial position of the ratchet shaft 228 following each incremental movement thereof. The locking beam 236 comprises a deflectable leaf spring which is normally biased into a position of engagement with ratchet shaft 228. A guide ring 240 is retained within an annular chamber 242 adjacent the secondary drive chamber 230 to ensure the stability of ratchet shaft 228 during its distal translation.

An elongated push rod 244 extends from the distalmost segment 228f of ratchet shaft 228 and is dimensioned and configured to translate through the axial bore 246 of needle body 204. Push rod 244 is positioned within an axial extension shaft 246 which depends from handle portion 202 and which is retained therein by mounting pins 248 and 250. Extension shaft 246 includes an elongated guide channel 252 through which push rod 244 translates, an internal chamber 254 for retaining the cinching member 20 of anchoring device 10, and a distal reception port 256 for mounting the proximal end 258 of needle body 204. The distal end portion 260 of needle body 204 depends angularly from the elongation thereof and defines a piercing point configured to extend through body tissue.

The sheath 206 is mounted coaxially with extension shaft 246 and is movable with respect thereto between a plurality of longitudinal positions to selectively expose the distal end portion 260 of needle body 204. A manipulation knob 262 (262a, 262b) is positioned adjacent the proximal end 264 of extension shaft 246 to position the sheath along the needle body 204. A transverse control pin 266 extends from manipulation knob 262, through an aperture 268 adjacent the proximal end 264 of sheath 206 to communicate with a guide track 270 defined in the outer wall 272 of extension shaft 246. Guide track 270 includes an elongated primary section 274 and a plurality of depending recessed areas 276a–276g within which control pin 266 may be selectively positioned to orient the sheath 206 in a desired longitudinal position.

In use, the sheath 206 may be moved relative to the extension shaft 246 by rotating the knob 262 relative to the longitudinal axis defined thereby to position control pin 266 within the primary section 274 of guide track 270. Thereupon, the sheath 206 may be moved along the length of the guide track 270 until a desired location is achieved, and then, the sheath 206 may be rotated to position the control pin 266 in a selected recessed area 276. When control pin 266 is positioned within the proximal most recessed area 276a, the distal portion 260 of needle body 204 is fully exposed by the sheath 206 (see FIG. 8). Conversely, when control pin 266 is positioned within the distal most recessed area 276g, the distal portion 260 of needle body 204 is fully shielded by sheath 206 (see FIG. 7).

Figure 11:
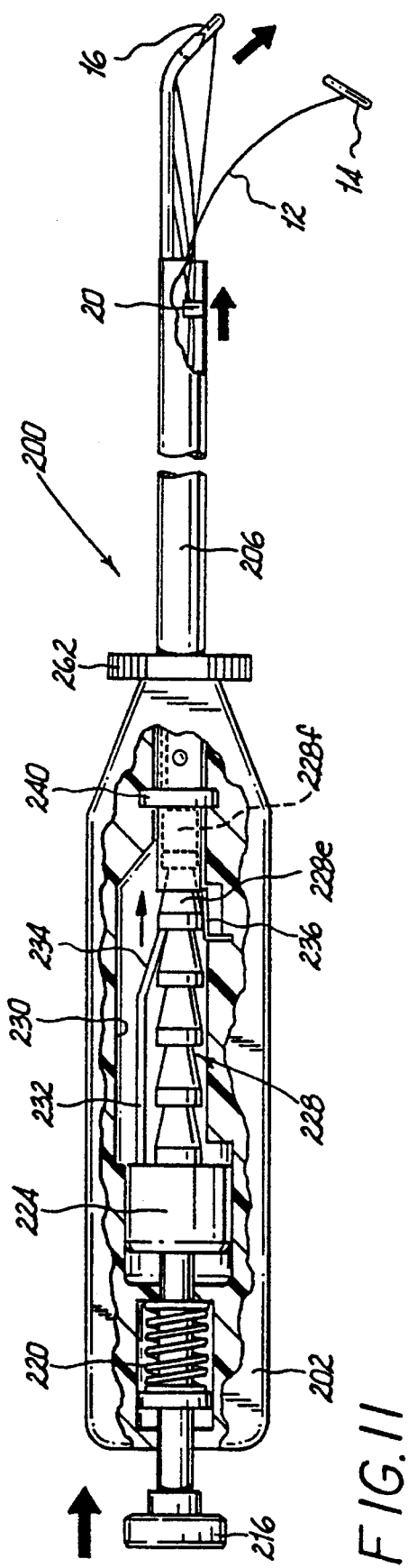
FIG. 11 is a side elevational view in partial cross-section of the anchor applying apparatus of FIG. 7 in a partially actuated position.
Figure 12:
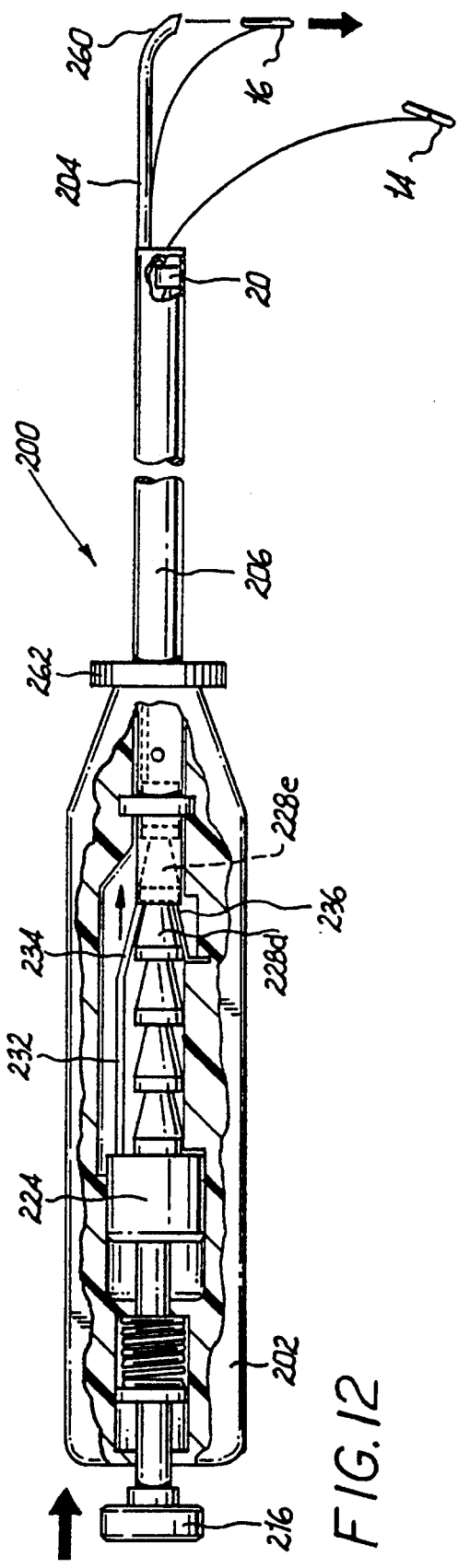
FIG. 12 is a side elevational view in partial cross-section of the anchor applying apparatus of FIG. 7 in a fully actuated position.
Figure 13:
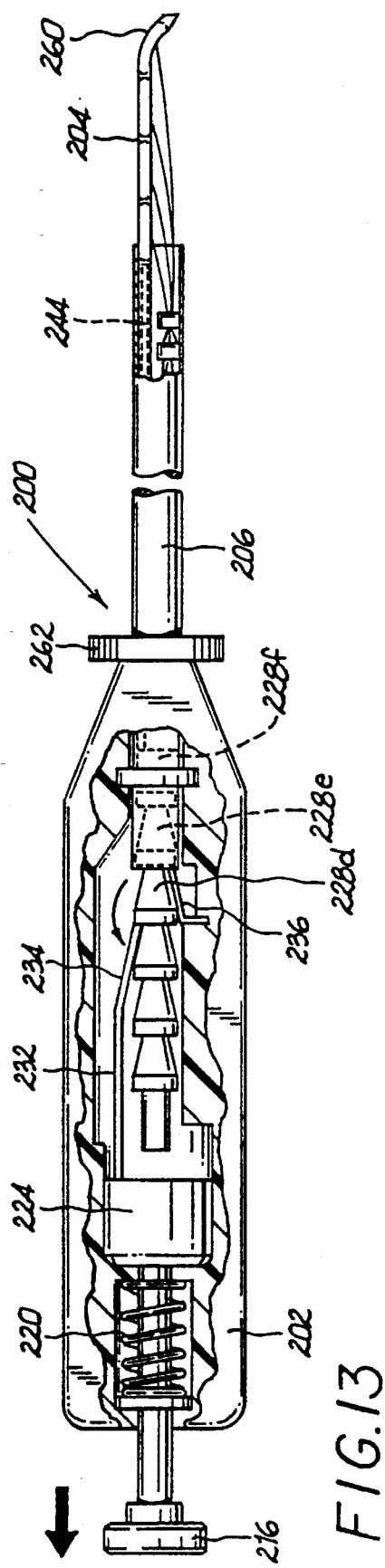
FIG. 13 is a side elevational view in partial cross-section of the anchor applying apparatus of FIG. 7 subsequent to actuation.

Referring now to FIGS. 10–13, there is illustrated a series of operational views of the surgical apparatus 200. In FIG. 13, the distal most ratchet segment 228f has been advanced by drive arm 232 and the first anchor 14 has been advanced from the distal end portion 260 of needle body 204. To deploy the second anchor 16 from the needle body 204, plunger 216 is moved in a distal direction against the bias of return spring 220 so as to urge drive shaft 224 forward within primary drive chamber 226, as shown in FIG. 11. As a consequence, drive arm 232, which is engaged behind ratchet segment 228e, urges ratchet shaft 228 in a distal direction through a distance which is equal to the length of segment 228e. Concomitantly, the push rod 244 advances distally, driving anchor 16 from the distal end portion 260 of needle body 204, as shown in FIG. 12. Subsequently, coiled spring 220 decompresses to return plunger 216 to a neutral position and position the distal end of drive arm 232 behind ratchet segment 228d. At such a time, locking beam 236 interacts with ratchet segment 228d to maintain its axial position.

Referring to FIGS. 14A and 14B, there is illustrated another embodiment of a surgical apparatus for applying the anchoring device 10 of the subject invention which is designated generally by reference numeral 280. Surgical apparatus 280 includes a handle portion 281 defining an internal cavity 282 dimensioned to house a two-stage actuation mechanism 283. The actuation mechanism 283 is configured to move an elongated needle body 284 relative to a sheath 285 and subsequently advance a push rod 286 through the needle body 284 to individually drive anchors 14 therefrom. The actuation mechanism 283 includes a spring biased plunger 287 which translates within a chamber 288 formed in an internal actuation sleeve 289 which is configured to translate within the cavity 282 defined in handle portion 281. A linear rachet assembly 290 which is substantially similar to that which is provided in surgical apparatus 200 is operatively associated with the internal actuation sleeve 289 and the plunger 287. The proximal end of needle body 284 extends from a guide tube 291 which is connected to the tapered end portion 292 of actuation sleeve 289, and the proximal end of push rod 285 extends from the distal end 290a of ratchet assembly 290.

In operation, partial compression of plunger 287 will cause corresponding distal movement of the needle body 284 relative to sheath 285 to penetrate through body tissue disposed within the tissue reception port 293 defined in sheath 285. The needle body 284 will continue to advance distally until the tapered end portion 292 of actuation sleeve 289 abuts against the forward buttressing wall 294 of cavity 282, as illustrated in FIG. 14B. At such a time, continued movement of plunger 287 will cause the linear ratchet mechanism 290 to advance distally relative to actuation sleeve 289. As a result, the push rod 285 will advance through the needle body 284 to urge the distalmost anchor member 14 therefrom. Subsequently, the plunger 287 will return to the prefired position illustrated in FIG. 14A.

IV. APPARATUS FOR DRAWING THE SUTURE

Referring to FIGS. 15A–16, a suture drawing apparatus constructed in accordance with a preferred embodiment of the subject invention is illustrated and is designated generally by reference numeral 300. As best seen in FIG. 16, apparatus 300 comprises a pair of telescopically associated members including an elongated inner control shaft 302 having a proximal end portion 304 and a distal end portion 306, and an elongated outer housing tube 308 having a proximal end portion 310 and a distal end portion 312. An axial manipulation handle 314 is positioned at the proximal end portion 304 of control shaft 302 and is mounted thereto by a pair of spaced apart set pins 316 and 318. A grasping handle 320 is provided at the proximal end portion 310 of housing tube 308 for maintaining the longitudinal position of the housing tube 308 as the inner control shaft 302 is moved with respect thereto.

An elongated guide slot 322 extends along a medial portion of control shaft 302 for communicating with a transverse guide pin 324 mounted adjacent the proximal end portion 310 of housing tube 308. The interaction of the guide slot 322 and the guide pin 324 serves to maintain the relative radial alignment of the inner control shaft 312 relative to the outer housing tube 308 with respect to the longitudinal axis defined thereby. In so doing, a suture drawn into the housing tube 308 by control shaft 302 will not become entangled.

A mounting slot 326 is formed at the distal end portion 306 of the inner control shaft 302 for receiving and retaining the shank portion 328 of an elongated grasping hook 330. The distal end 332 of grasping hook 330 depends angularly from the elongation thereof and is dimensioned and configured to engage the looped portion 40 of the suture 12 of anchoring device 10. In operation, as best seen in FIG. 15B, a suture may be drawn into the outer housing tube 308 of surgical apparatus 300 by retracting the inner control shaft 302 into the outer housing tube 308, while maintaining the longitudinal position of the outer housing tube 308 by holding grasping handle 320. The distance that the suture may be drawn into housing tube 308 will be limited by the length of the guide slot 322 in control shaft 302.

V. THE URETHROVESICAL ELEVATION PROCEDURE

Referring to FIGS. 17–21, a series of sagittal sections taken through the pelvic region of a female are provided which illustrate the operational steps of the method of the subject invention. While the following method is directed to a method for urethrovesical elevation, it should be noted that the procedure is exemplary, and that other applications of the sutured anchor devices may be utilized in a manner to either suspend, retract, approximate or otherwise position tissue or organs relative to one another. One example of such a procedure is closure of an incision, such as fascia, which would involve placing one anchor of an anchoring device through a first side of the incision and then placing the second anchor of the suture anchoring device through the second opposed side of the incision. With the two anchors of the device adjacently emplaced, the cinching member is engaged by the apparatus for adjusting the operative length of the anchoring device. The apparatus for adjusting the operative length would engage the looped portion of the suture and effects relative movement of the suture and cinching member to vary the length of the suture and thereby approximate the ends thereof and approximate the opposed incision sides. In fascia closure, the anchoring device may also be used in conjunction with a biocompatible washer which would be applied around the suture between the anchors 14, 16 and the structure through which the anchors have been inserted to distribute the force or compression that the anchors are subjected to.

In each figure, the anatomical structures related to the subject procedure will be designated by the following numbering convention: the retropubic space 400; the vagina 402 including the vaginal wall 404 having an interior surface 406 and an exterior surface 408; the bladder 410; the urethra 412; the urethrovesical junction or the bladder neck 414; Cooper's ligament or the pectineal ligament 416 having a posterior surface 418 and an anterior surface 420; the pubic bone 422; and the abdominal wall 424 including the skin 426 and subcutaneous fat 428.

Figure 17:
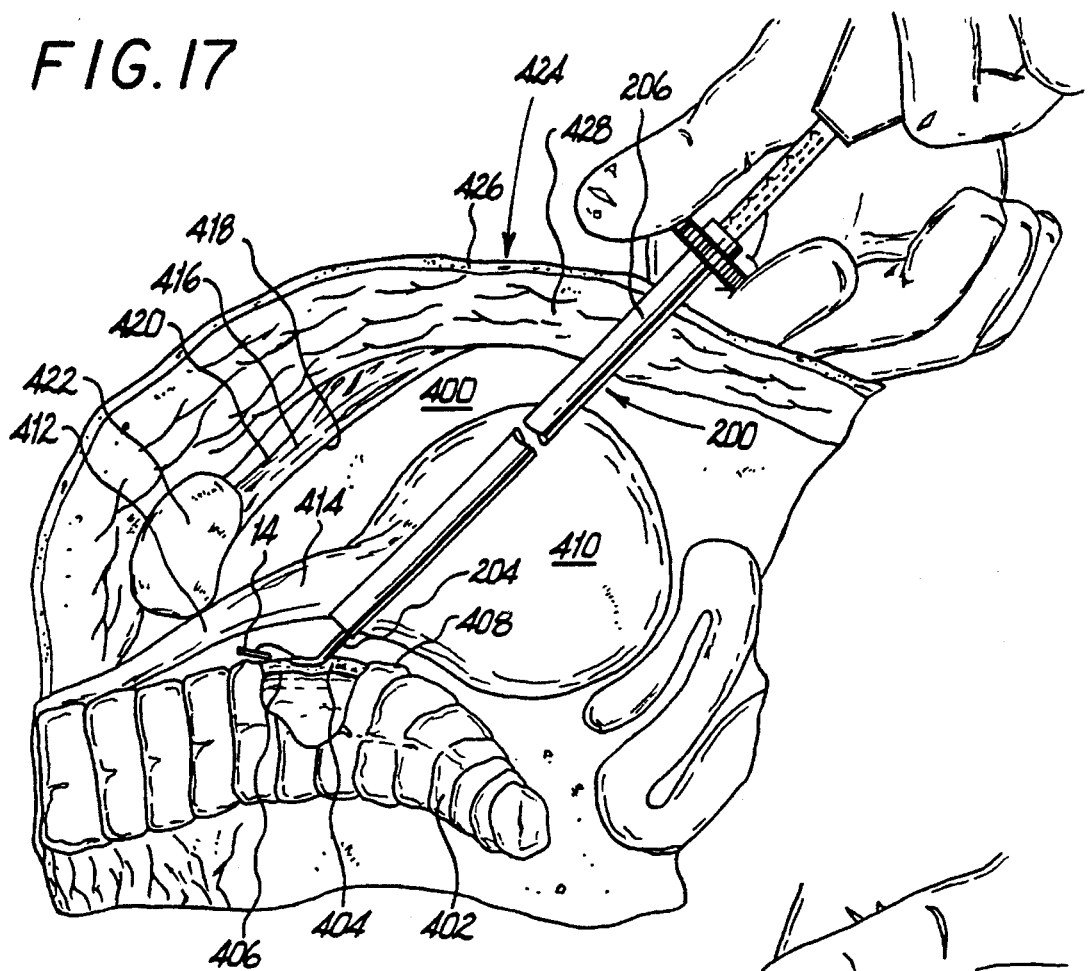
FIG. 17 is a sagittal section taken through the pelvic region of a female illustrating the anchor applying apparatus of FIG. 7 emplacing the first anchor of the anchoring device of FIG. 1 in the vaginal wall.

Referring now to FIG. 17, initially the anchor applying apparatus 200 is extended through the abdominal wall 424 to introduce the instrument into the retropubic space 400. The introduction can be made through a small incision or through a trocar or cannula device inserted into the abdomen. Once inside the retropubic space 400, the distal end portion of the needle body 204 is directed toward the exterior surface 408 of the vagina 402. The needle body 204 is then inserted into the vaginal wall 404 and subsequently extended from the vaginal wall 404 at a location spaced from the point of insertion. At such a time, the first anchor 14 disposed at the end of suture 12 is advanced from the distal end of the needle body 204 and emplaced adjacent the exterior surface 408 of the vaginal wall 404, thereby securing the first anchor 14 to the vaginal wall 404.

Figure 18:
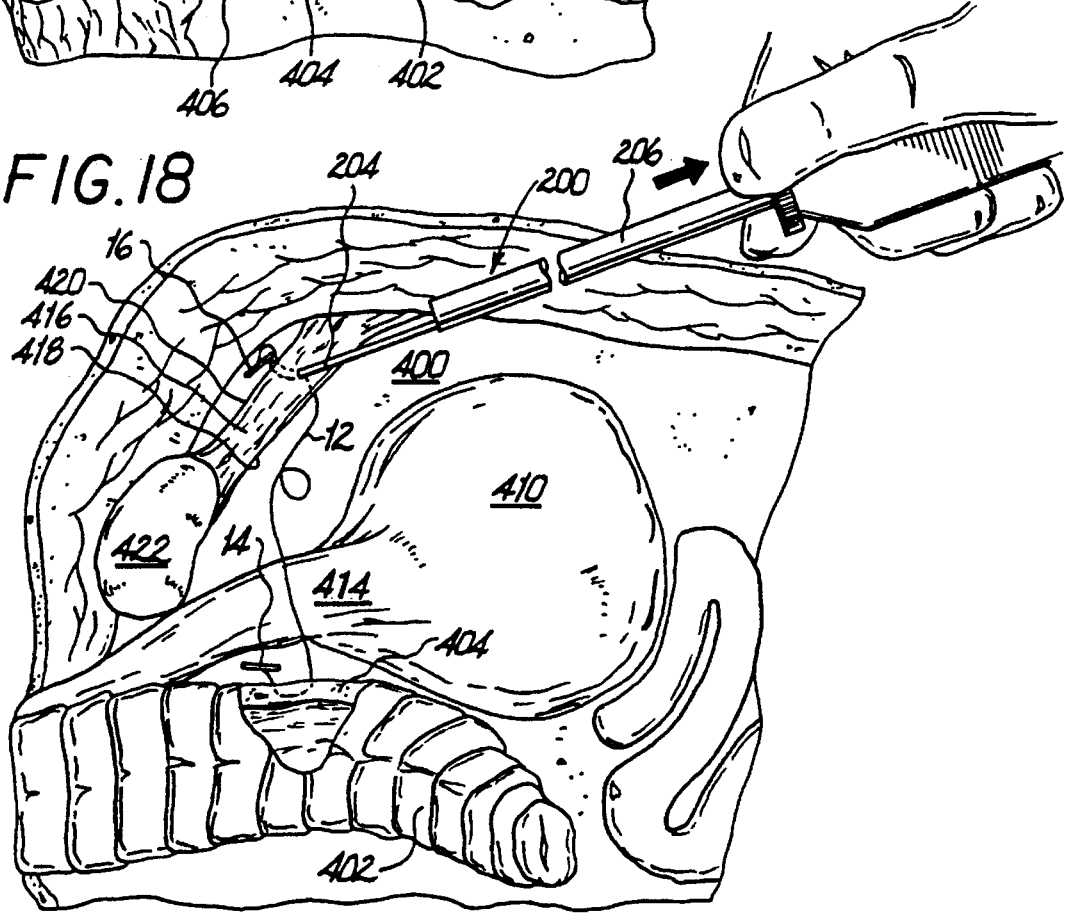
FIG. 18 is a sagittal section illustrating the application of the second anchor of the anchoring device of FIG. 1 in Cooper's ligament.

Referring now to FIG. 18, to secure the second anchor 16 at the opposed end of suture 12 to Cooper's ligament, the anchor applying device 200 is initially directed toward Cooper's ligament 416. Then, the distal end of the needle body 204 is extended through Cooper's ligament 416 from the posterior surface 418 thereof to the anterior surface 420 thereof. Thereupon, the second anchor 16 is advanced from the distal end of the needle body 204 and emplaced adjacent the interior surface 420 of Cooper's ligament, thereby securing the second anchor 16 to Cooper's ligament. At such a time, the anchor applying apparatus 200 may be withdrawn from the retropubic space 400 through the abdominal wall 424. As apparatus 200 is withdrawn, the cinching member 20 egresses from the housing 206 and remains within the retropubic space 400.

Figure 19:
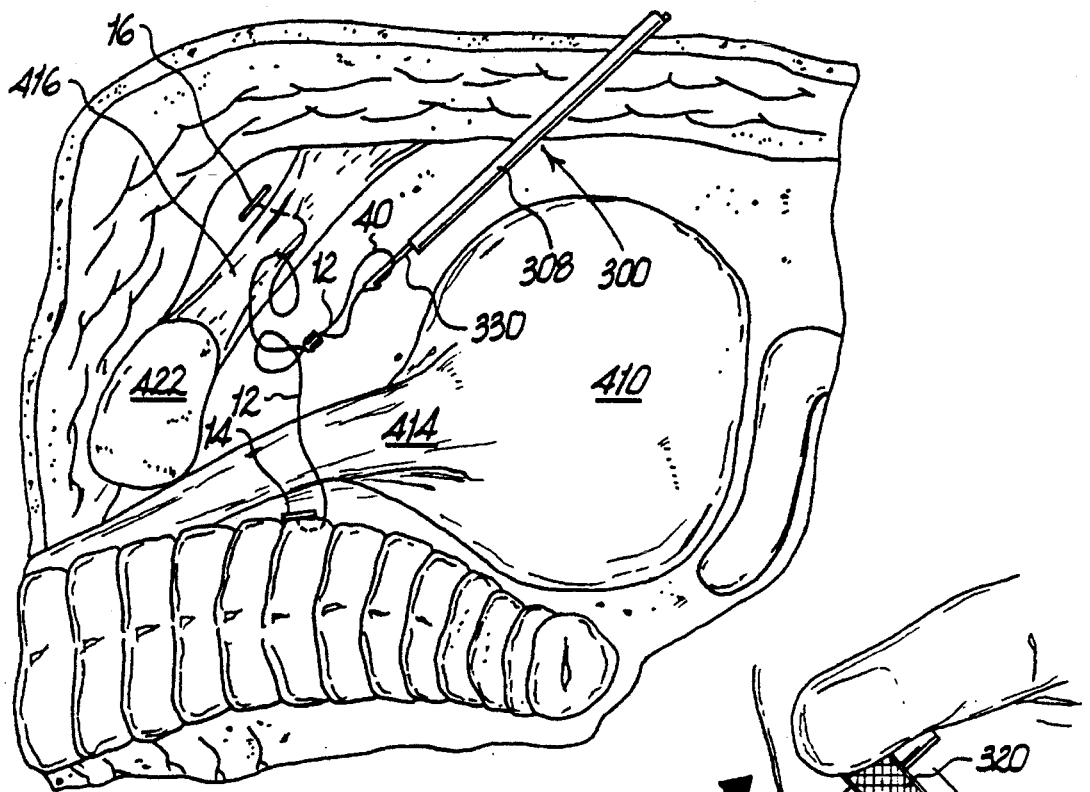
FIG. 19 is a sagittal section illustrating the engagement of the suture of the anchoring device of FIG. 1 by the anchor device adjusting apparatus of FIG. 15A.

Referring now to FIG. 19, following the removal of anchor applying apparatus 200 from the surgical site, the suture drawing apparatus 300 is introduced into the retropubic space 400 through the abdominal wall 424. The introduction will preferably occur through the same incision through which apparatus 200 was introduced. Once inside the retropubic space 400, the grasping hook 330 provided at the distal end of inner control shaft 302 is directed toward the anchoring device 10. Subsequently, the loop 40 formed in suture 12 is engaged by the distal end 332 of hook 330.

Figure 20:
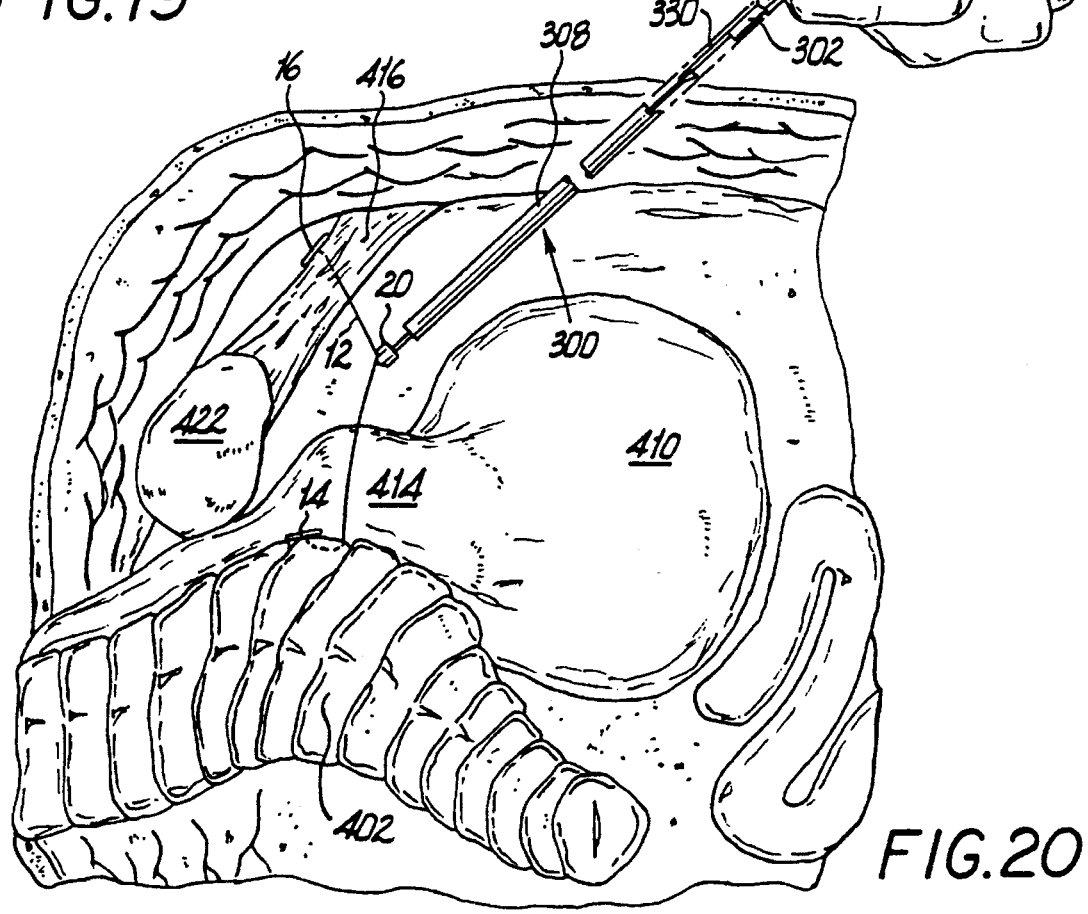
FIG. 20 is a sagittal section illustrating the drawing of the suture relative to the cinching member by the anchor device adjusting apparatus of FIG. 15A to move the vaginal wall and Cooper's ligament into juxtaposition.
Figure 21:
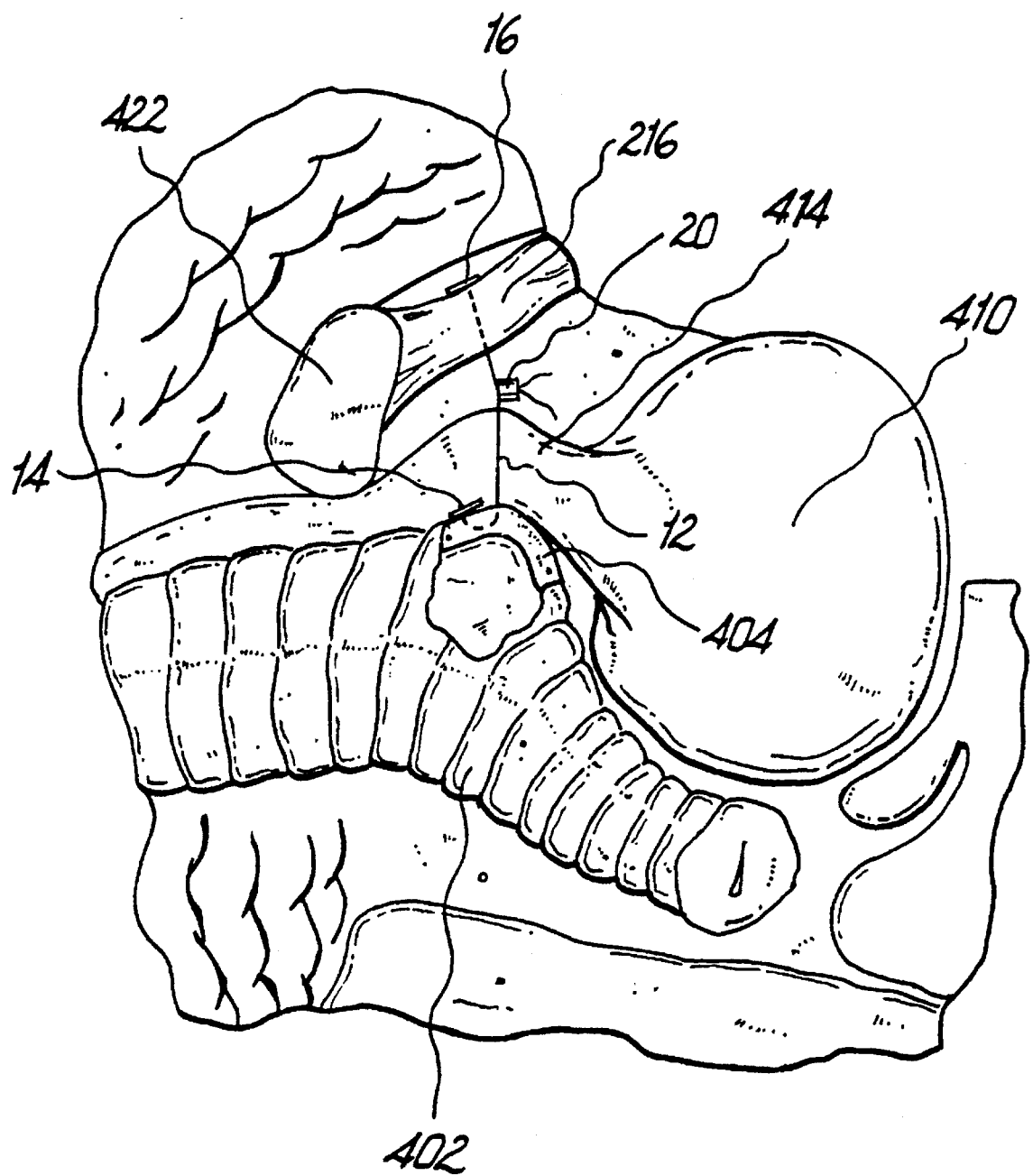
FIG. 21 is a sagittal section illustrating the urethrovesical junction elevated relative to the bladder as a result of the approximation of the first and second anchors with respect to one another.

Then, as illustrated in FIG. 20, the control shaft 302 is retracted into the outer housing tube 308, drawing suture 12 therewith. As suture 12 is drawn into housing tube 308, the cinching member 20 is brought into contact with the distal end thereof and is maintained thereagainst as the suture 12 is drawn relative the cinching member 20. As a result, the first and second anchors 14 and 16 are approximated toward one another, thereby moving the vaginal wall 404 into juxtaposition with Cooper's ligament 416 so as to elevate the urethrovesical junction or bladder neck 414 relative to the bladder 410 as illustrated in FIG. 21. Once the bladder neck 414 has been elevated, the involuntary escape of urine under conditions of increased intra-abdominal pressure is effectively inhibited.

Following the initial application of the anchoring device 10, if required, additional anchoring devices may be applied to the vaginal wall and Cooper's ligament. In total, three anchoring devices are retained within the anchor applying apparatus 200 for ready application to body tissue.

VI. THE KIT

Figure 22:
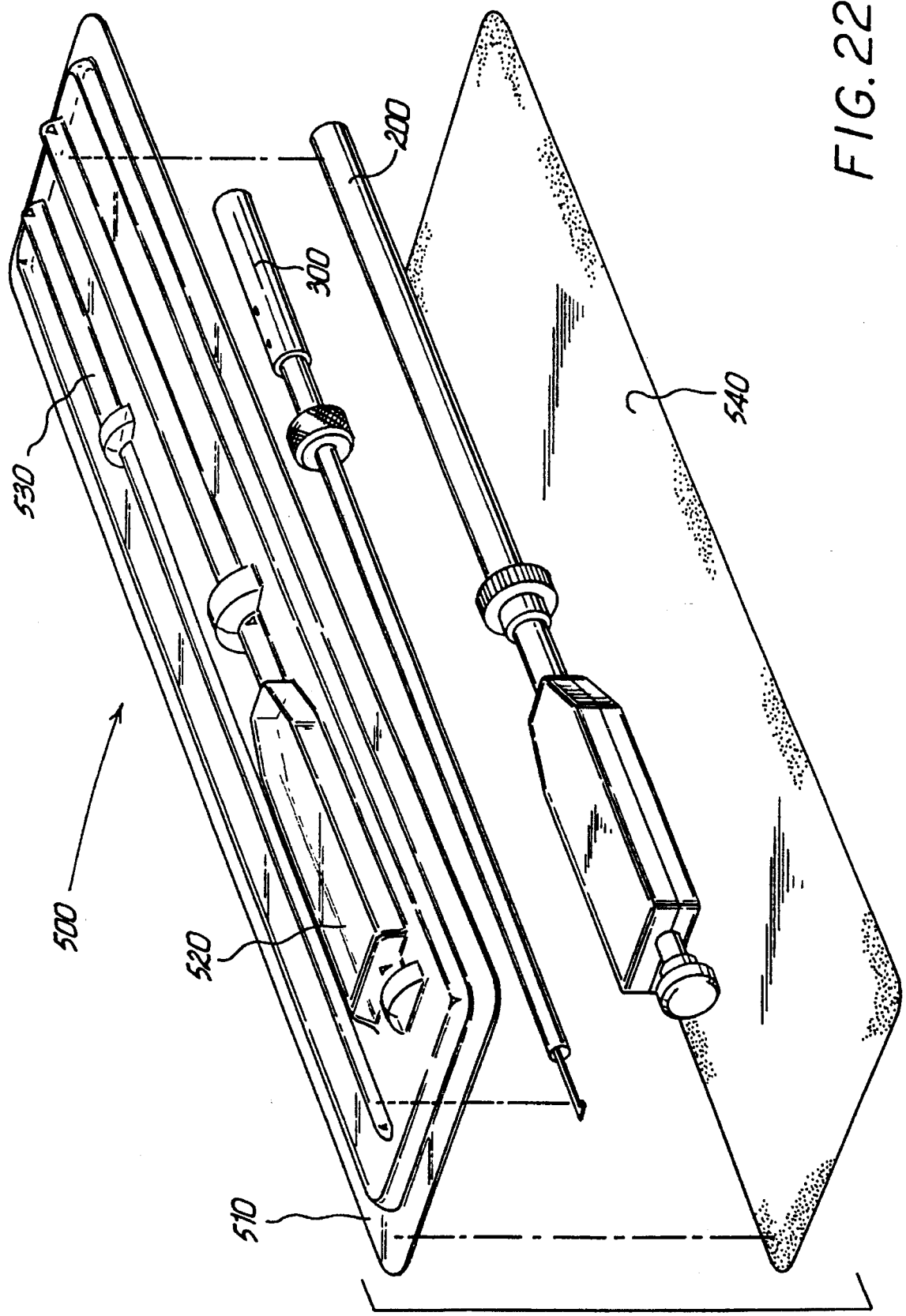
FIG. 22 is a plan view of an enclosure or kit containing the anchor applying apparatus of FIG. 7 and the anchor device adjusting apparatus of FIG. 15A.

Referring to FIG. 22, a kit containing the apparatus necessary to perform the procedure of the subject invention is illustrated and is designated generally by reference numeral 500. The kit comprises a preformed enclosure 510 defining recessed areas 520 and 530 for respectively retaining the apparatus 200 for applying the anchoring device 10, and the apparatus 300 for drawing the suture 12 relative to the cinching member 20. The enclosure is preferably vacuum formed from a durable plastic material and is configured to be hermetically sealed with a cover sheet 540 to maintain the sterility of the instrumentation enclosed therein.

Although the subject invention has been described with respect to a preferred embodiment, it will be readily apparent to those having ordinary skill in the art to which it appertains that changes and modifications may be made thereto without departing from the spirit or scope of the subject invention as defined by the appended claims.

What is claimed is:

1. An apparatus for applying a surgical anchoring device to body tissue, said anchoring device including an elongated suture having an anchor member positioned at each end thereof, said apparatus comprising:

a) a handle portion defining a longitudinal axis;

b) an elongated needle body extending from said handle portion and defining an axial bore configured to consecutively retain the anchor members;

c) an elongated housing mounted adjacent said needle body, said needle body and said elongated housing being relatively movable between a plurality of longitudinal positions to selectively extend and retract said distal end portion of said needle body; and d) a ratchet assembly operatively associated with said handle portion for individually axially advancing the anchor members from said distal end portion of said needle body, said ratchet assembly including an axially advanceable rack, a push rod extending from the rack and configured to incrementally advance through the needle body to urge the anchor members therefrom, and an axially advanceable drive arm for selectively engaging the rack.

2. An apparatus as recited in claim 3, wherein said elongated housing is configured for incremental movement between a plurality of longitudinally oriented positions to selectively expose and shield said distal end portion of said needle body.

3. An apparatus for applying a surgical anchoring device to body tissue, said anchoring device including an elongated suture having an anchor member positioned at each end thereof, said apparatus comprising:

a) a handle portion defining a longitudinal axis;

b) an elongated needle body extending from said handle portion and defining an axial bore configured to retain the anchor members, said needle body having a continuous uniform cross-sectional configuration;

c) an elongated housing mounted adjacent said needle body and longitudinally movable with respect thereto between a first position wherein a distal end portion of said needle body is extended from said housing and a second position wherein said distal end portion of said needle body is shielded by said housing; and d) means operatively associated with said handle portion for individually advancing the anchor members from said distal end portion of said needle body, the advancing means including an axially advanceable rack member, a push rod extending from the rack and configured to incrementally advance through the needle body to urge the anchor members therefrom, and an axially advanceable drive arm for selectively engaging the rack member.

4. An apparatus as recited in claim 3, wherein said distal end portion of said needle body depends angularly from the longitudinal axis thereof.

5. An apparatus as recited in claim 3, wherein said means for individually advancing said anchor members further includes an engaging beam for locking said rack member in a predetermined axial position.

6. An apparatus as recited in claim 5, wherein said driving arm is normally biased in a proximal direction by a coiled biasing spring disposed coaxial with said ratchet assembly.

7. An apparatus as recited in claim 5, wherein said engaging beam comprises a cantilevered leaf spring disposed in said handle portion adjacent said rack member.

8. An apparatus as recited in claim 3, wherein said elongated housing is dimensioned and configured for endoscopic utilization.

9. An apparatus for applying a surgical anchoring device to body tissue, said anchoring device including an elongated suture having an anchor member positioned at each end thereof, said apparatus comprising:

a) a handle portion defining a longitudinal axis;

b) an elongated needle body extending from said handle portion and defining an axial bore configured to retain the anchor members;

c) an elongated housing mounted adjacent said needle body and incrementally movable with respect thereto between a plurality of longitudinal positions to selectively protract said distal end portion of said needle body from said housing; and d) an axially advanceable ratchet assembly operatively associated with said handle portion for individually advancing the anchor members from said distal end portion of said needle body, the ratchet assembly including an axially advanceable rack, a push rod extending from the rack and configured to incrementally advance through the needle body to urge the anchor members therefrom, and an axially advanceable drive arm for selectively engaging the rack and advancing the rack in a distal direction.

10. An apparatus as recited in claim 9, wherein said axially advanceable ratchet assembly further includes an engaging beam for locking said rack member in a predetermined axial position.

11. An apparatus as recited in claim 9, wherein said driving arm is normally biased in a proximal direction by a coiled biasing spring, and said engaging beam comprises a cantilevered leaf spring disposed adjacent said rack member.

12. An apparatus as recited in claim 9, wherein said elongated housing is dimensioned and configured for endoscopic utilization.

13. An apparatus for applying a surgical anchoring device to body tissue, said anchoring device including an elongated suture having an anchor member positioned at each end thereof, said apparatus comprising:

a) a handle portion defining a longitudinal axis;

b) an elongated needle body extending from said handle portion and defining an axial bore configured to consecutively retain the anchor members;

c) an elongated housing mounted adjacent said needle body and defining opposed proximal and distal ends and means for receiving tissue disposed between said opposed proximal and distal ends; and d) actuation means operatively associated with said handle portion for advancing said needle body in a distal direction relative to said housing and for advancing a distalmost anchor member in a distal direction from a distal end of said needle body, the actuation means including an axially advanceable rack, a push rod extending from the rack and configured to incrementally advance through the needle body to urge the anchor members therefrom and an axially advanceable drive arm for selectively engaging the rack.

14. An apparatus as recited in claim 13, wherein said means for receiving tissue comprises a tissue reception port defined in said housing adjacent a distal end thereof and communicating with the distal end of said needle body.

* * * * *

UNITED STATES PATENT AND TRADEMARK OFFICE
CERTIFICATE OF CORRECTION

PATENT NO. : 5,507,754
DATED : April 16, 1996
INVENTOR(S) : David T. Green, Henry R. Sienkiewicz, Keith Ratcliff, Salvatore Castro and Scott E. Manzo It is certified that error appears in the above-indentified patent and that said Letters Patent is hereby corrected as shown below:

Cancel Figs. 6A, 6B, 16A, 16B, 16C, 16D, 16E and 16F.

Redesignate Fig. 15C as Fig. 16.

Signed and Sealed this

Eighteenth Day of February, 1997

Attest:

BRUCE LEHMAN

Attesting Officer

Commissioner of Patents and Trademarks